(12) United States Patent
Rooney et al.

(10) Patent No.: US 8,204,607 B2
(45) Date of Patent: Jun. 19, 2012

(54) IMPLANTABLE MEDICAL LEAD

(75) Inventors: Ethan A. Rooney, White Bear Lake, MN (US); Carl D. Wahlstrand, Lino Lakes, MN (US); Gary W. King, Fridley, MN (US); Thomas E. Cross, Jr., St. Francis, MN (US); Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 939 days.

(21) Appl. No.: 11/450,148

(22) Filed: Jun. 9, 2006

(65) Prior Publication Data
US 2007/0150034 A1 Jun. 28, 2007

Related U.S. Application Data

(63) Continuation-in-part of application No. 11/374,852, filed on Mar. 14, 2006, now Pat. No. 7,813,803, and a continuation-in-part of application No. 11/375,492, filed on Mar. 14, 2006, now Pat. No. 7,890,166, and a continuation-in-part of application No. 11/374,793, filed on Mar. 14, 2006.

(60) Provisional application No. 60/689,168, filed on Jun. 9, 2005, provisional application No. 60/700,627, filed on Jul. 19, 2005, provisional application No. 60/761,823, filed on Jan. 25, 2006.

(51) Int. Cl.
*A61N 1/36* (2006.01)
(52) U.S. Cl. ...................................... 607/130
(58) Field of Classification Search .................. 607/118, 607/130, 131
See application file for complete search history.

(56) References Cited

U.S. PATENT DOCUMENTS

| 3,211,151 A | 10/1965 | Foderick et al. |
| 3,385,300 A | 5/1968 | Holter |
| 3,738,368 A | 6/1973 | Avery et al. |

(Continued)

FOREIGN PATENT DOCUMENTS

DE 197 58 114 7/1999

(Continued)

OTHER PUBLICATIONS

Kapural et al, "Occipital Nerve Electrical Stimulation via the Midline Approach and Subcutaneous Surgical Leads for Treatment of Severe Occipital Neuralgia: A Pilot Study," Anesthesia Analgesia 2005; 101, pp. 171-174.

(Continued)

*Primary Examiner* — Scott Getzow
*Assistant Examiner* — Amanda Patton
(74) *Attorney, Agent, or Firm* — Shumaker & Sieffert, P.A.

(57) ABSTRACT

The disclosure describes an implantable medical lead for delivering stimulation to a patient. Electrodes may be located on two or more surfaces of the lead to, for example, selectively deliver stimulation to one or more tissue layers within the patient. The lead may be implanted within or between intra-dermal, deep dermal, or subcutaneous tissue layers, and may be used to, for example, deliver peripheral nerve field stimulation to treat pain experienced by the patient at the site at which the lead is implanted. The lead may comprise a paddle lead or a multiple level lead, e.g., a lead having a plurality of flat or paddle shaped lead bodies arranged in substantially parallel planes. Further, the lead may include fixation structures on the distal end, proximal end, or both ends to prevent migration.

7 Claims, 14 Drawing Sheets

U.S. PATENT DOCUMENTS

| | | | |
|---|---|---|---|
| 3,978,865 A * | 9/1976 | Trabucco | 607/9 |
| 4,058,128 A * | 11/1977 | Frank et al. | 607/130 |
| 4,140,131 A | 2/1979 | Dutcher et al. | |
| 4,142,530 A * | 3/1979 | Wittkampf | 607/116 |
| 4,144,889 A * | 3/1979 | Tyers et al. | 607/130 |
| 4,177,818 A * | 12/1979 | De Pedro | 607/130 |
| 4,658,835 A | 4/1987 | Pohndorf | |
| 4,759,748 A | 7/1988 | Reed | |
| 5,300,110 A * | 4/1994 | Latterell et al. | 607/130 |
| 5,545,207 A * | 8/1996 | Smits et al. | 607/130 |
| 5,645,062 A | 7/1997 | Anderson et al. | |
| 5,792,187 A | 8/1998 | Adams | |
| 5,843,148 A | 12/1998 | Gijsbers et al. | |
| 5,897,583 A | 4/1999 | Meyer et al. | |
| 6,038,480 A | 3/2000 | Hrdlicka et al. | |
| 6,058,331 A | 5/2000 | King | |
| 6,249,707 B1 * | 6/2001 | Kohnen et al. | 607/117 |
| 6,381,496 B1 * | 4/2002 | Meadows et al. | 607/59 |
| 6,473,653 B1 | 10/2002 | Schallhorn et al. | |
| 6,510,347 B2 * | 1/2003 | Borkan | 607/117 |
| 6,517,477 B1 | 2/2003 | Wendlandt | |
| 6,735,475 B1 | 5/2004 | Whitehurst et al. | |
| 6,978,180 B2 | 12/2005 | Tadlock | |
| 7,010,345 B2 | 3/2006 | Hill et al. | |
| 7,120,495 B2 | 10/2006 | Bardy et al. | |
| 7,181,288 B1 * | 2/2007 | Rezai et al. | 607/116 |
| 2002/0103510 A1 | 8/2002 | Bardy et al. | |
| 2002/0107553 A1 | 8/2002 | Hill et al. | |
| 2002/0143369 A1 | 10/2002 | Hill et al. | |
| 2002/0183817 A1 | 12/2002 | Van Venrooij et al. | |
| 2002/0198572 A1 | 12/2002 | Weiner | |
| 2003/0004549 A1 | 1/2003 | Hill et al. | |
| 2003/0078633 A1 | 4/2003 | Firlik et al. | |
| 2003/0105501 A1 | 6/2003 | Warman et al. | |
| 2003/0144709 A1 | 7/2003 | Zabara et al. | |
| 2003/0212445 A1 | 11/2003 | Weinberg | |
| 2004/0015204 A1 | 1/2004 | Whitehurst et al. | |
| 2004/0059348 A1 | 3/2004 | Geske et al. | |
| 2004/0098074 A1 * | 5/2004 | Erickson et al. | 607/117 |
| 2004/0122477 A1 | 6/2004 | Whitehurst et al. | |
| 2004/0176830 A1 * | 9/2004 | Fang | 607/129 |
| 2004/0243205 A1 * | 12/2004 | Keravel et al. | 607/116 |
| 2005/0015117 A1 | 1/2005 | Gerber | |
| 2005/0070969 A1 | 3/2005 | Gerber | |
| 2005/0222628 A1 | 10/2005 | Krakousky | |
| 2005/0246006 A1 | 11/2005 | Daniels | |
| 2005/0256452 A1 | 11/2005 | DeMarchi et al. | |
| 2006/0030899 A1 | 2/2006 | O'Keeffe et al. | |
| 2006/0270978 A1 | 11/2006 | Binmoeller et al. | |
| 2006/0271137 A1 | 11/2006 | Stanton-Hicks | |
| 2007/0027514 A1 * | 2/2007 | Gerber | 607/116 |
| 2007/0118196 A1 | 5/2007 | Rooney et al. | |

FOREIGN PATENT DOCUMENTS

| | | |
|---|---|---|
| GB | 2 274 995 | 8/1994 |
| WO | WO 01/89626 | 11/2001 |
| WO | WO 02/34330 | 5/2002 |
| WO | WO 02/068042 | 9/2002 |
| WO | WO 03/026736 | 4/2003 |
| WO | WO 03/047687 | 6/2003 |
| WO | WO 2004/012812 | 2/2004 |

OTHER PUBLICATIONS

Notification of Transmittal of the International Search Report and the Written Opinion for corresponding PCT Application No. PCT/US2006/022721 dated Nov. 6, 2006 (12 pgs.).

Reply to Written Opinion for corresponding PCT Application No. PCT/US2006/022721, dated Apr. 9, 2007 (11 pgs.).

Notification of Transmittal of the International Preliminary Report on Patentability for corresponding PCT Application No. PCT/US2006/022721, dated Jun. 6, 2007 (11 pgs.).

U.S. Appl. No. 11/450,133, filed Jun. 9, 2006, entitled "Combination Therapy Including Peripheral Nerve Field Stimulation."

U.S. Appl. No. 11/450,127, filed Jun. 9, 2006, entitled "Implantable Medical Device with Electrodes on Multiple Housing Surfaces."

U.S. Appl. No. 11/450,147, filed Jun. 9, 2006, entitled "Introducer for Therapy Delivery Elements."

U.S. Appl. No. 11/450,144, filed Jun. 9, 2006, entitled "Peripheral Nerve Field Stimulation and Spinal Cord Stimulation."

U.S. Appl. No. 11/374,852, filed Mar. 14, 2006, entitled "Regional Therapies for Treatment of Pain."

U.S. Appl. No. 11/375,492, filed Mar. 14, 2006, entitled "Regional Therapies for Treatment of Pain."

U.S. Appl. No. 11/374,793, filed Mar. 14, 2006, entitled "Regional Therapies for Treatment of Pain."

European Office Action dated Sep. 22, 2008 for Application No. 06760740.8-2319 (2 pgs.).

Office Action dated Oct. 6, 2009 for U.S. Appl. No. 11/450,127 (7 pgs.).

Responsive Amendment dated Jan. 6, 2010 for U.S. Appl. No. 11/450,127 (9 pgs.).

* cited by examiner

IMPLANTABLE MEDICAL LEAD

This application claims the benefit of U.S. Provisional Application No. 60/689,168, filed Jun. 9, 2005. This application is also a continuation-in-part of each of U.S. application Ser. No. 11/374,852, filed on Mar. 14, 2006, Ser. No. 11/375,492, filed on Mar. 14, 2006, and Ser. No. 11/374,793, filed on Mar. 14, 2006, each of which claims the benefit of U.S. Provisional Application Nos. 60/700,627, filed on Jul. 19, 2005, and 60/761,823, filed on Jan. 25, 2006. The entire content of each of these applications is incorporated herein by reference.

TECHNICAL FIELD

The invention relates to implantable medical devices and, more particularly, to implantable leads for delivery of electrical stimulation.

BACKGROUND

Electrical stimulation may be delivered to a patient to treat a variety of symptoms or disorders, such as chronic or episodic pain, gastrointestinal disorders, or pelvic floor disorders. Transcutaneous electrical nerve stimulation (TENS), percutaneous electrical nerve stimulation (PENS), peripheral nerve stimulation (PNS), spinal cord stimulation (SCS), deep brain stimulation (DBS) and cortical stimulation (CS) are examples of electrical stimulation therapies that have proved effective in treating, for example, pain, movement disorders, epilepsy, or other neurological disorders. Stimulation of the gastrointestinal tract can be effective in alleviating gastroparesis and obesity. Stimulation of the sacral nerves, pudendal nerves, or other nerves or tissues associated with the pelvic floor can be effective in alleviating urinary incontinence, fecal incontinence, pelvic pain, and sexual dysfunction.

Many electrical stimulation therapies are delivered by an implantable medical device, e.g., an implantable pulse generator, which is chronically implanted within the patient. One or more implantable leads extending from the implantable medical device carry electrodes for delivery of stimulation energy to a target nerve. For example, leads may be implanted proximate to the spinal cord, pelvic nerves, stomach, gastrointestinal tract, or within the cranium of a patient, e.g., for DBS or CS. The number and positions of the leads and electrodes within the patient is largely dependent on type of stimulation therapy and symptom or disorder treated. Leads and electrodes that deliver SCS, DBS, CS, gastrointestinal stimulation, and pelvic floor stimulation are generally surgically implanted, e.g., via laminectomy, or inserted percutaneously.

A lead typically carries one or more electrodes, e.g., ring electrodes, pad electrodes, or cuff electrodes, disposed at or near the distal end of the lead. Ring electrodes typically extend about the circumference of a lead, and are positioned at respective axial positions along a length of the distal end of the lead. "Paddle leads" typically include a substantially flat insulating body at their distal end, which may have a rectangular solid or otherwise "paddle-like" three-dimensional shape. One surface of the body or "paddle" at the distal end of the paddle lead carries a one or two-dimensional array of pad electrodes. Pad electrodes are substantially flat, three-dimensional conductors, e.g., having a substantially circular cross-section, which may be formed on or attached to the single surface of the paddle. Cuff electrodes are generally embedded within a self-curling or manipulable cuff designed to fit accurately around a specific target peripheral nerve, and are exposed only on the interior surface of the cuff.

In general, the stimulation therapies identified above are delivered to one or more specific target nerves or nerve structures, and may be delivered via leads and electrodes configured to direct stimulation to those particular nerves or nerve structures, and avoid stimulation of other tissues. For example, SCS involves stimulation the spinal cord from within the epidural space at specific targeted locations, such as near vertebral levels T8-T10 to treat axial back pain, over the dorsal columns at vertebral levels T10-L1 to treat pain in the back, legs, ankles or feet, or over the dorsal roots, i.e., proximal to dorsal root entry zone, of L3-S1. Delivering stimulation to the appropriate location on the spinal cord causes paresthesia in the area of perceived pan and may be most effective for neuropathic pain, such as neuropathy or radiculopathy that involves a significant portion of one limb and more than one dermatome.

As another example, PNS involves delivery of stimulation to a specific peripheral nerve via one or more electrodes implanted proximate to or in contact with a peripheral nerve, e.g., cuff electrodes surrounding the peripheral nerve or electrodes on one surface of a flat paddle lead placed in very close proximity to or contact with the nerve. Placing electrodes in very close proximity to the nerve may ensure that only fibers within that nerve are activated at low amplitudes.

For treatment of pain with PNS, the electrodes are implanted in close proximity to the nerve "upstream" from the source of damage or pain, e.g., closer to the spinal cord than the region of damage or pain. When electrodes are implanted upstream, the paresthesia resulting from PNS may extend to a broader area innervated by the target peripheral nerve. The most common upper extremity nerves treated with PNS are the ulnar nerve, median nerve, radial nerve, tibial nerve and common peroneal nerve.

SUMMARY

In general, the invention is directed to an implantable medical lead comprising a lead body with multiple surfaces. In some embodiments, electrodes are located on two or more surfaces of the lead body. Delivery of stimulation via electrodes on multiple surfaces of the lead may allow delivery stimulation to a variety of tissues proximate to the lead, and with a variety of current field configurations.

The multiple surfaces may include first and second opposed and/or substantially parallel surfaces, which may be located at different tissue depths when implanted in a patient. For example, the lead may be paddle lead with a substantially flat paddle-shaped distal lead body, and electrodes or electrode surfaces on the substantially parallel and opposed top and bottom surfaces of the paddle-shaped distal end. In other embodiments, the lead may be a multiple level lead, e.g., a lead having lead body with a plurality of paddle-shaped lead body levels arranged in substantially parallel planes. Each of the levels may include electrodes on one or more surfaces of the level.

Stimulation delivered via opposed, e.g., top and bottom, surfaces of the lead body may stimulate tissue located deeper and shallower than lead. Stimulation delivered via adjacent surfaces of adjacent levels in a multi-level lead may stimulate tissue between the levels. The lead may be implanted within or between intra-dermal, deep dermal, or subcutaneous tissue layers of the patient, and may deliver stimulation to any one or more of these layers In some embodiments, electrodes on different surfaces may be in electrical contact e.g., from the top surface to the bottom surface. In this manner, the electrodes may be used to deliver stimulation simultaneously to different tissues or tissue layers proximate to the different surfaces, e.g., to tissues deeper than the implanted lead and shallower than the implanted lead. In other embodiments, the electrodes positioned on different surfaces may be electrically isolated from each other so that the electrodes may be used to selectively deliver stimulation to different tissues or tissue layers proximate to the surfaces. The electrodes may be, for example, pad electrodes.

The lead may include one or more fixation structures on the distal end, proximal end, or both ends of a distal lead body to prevent movement of the lead body within the patient after implantation. Migration of the lead from the implantation site may result in a loss of the therapeutic efficacy of the delivered stimulation, e.g., loss of paresthesia, or the emergence of side effects resulting from delivery of the stimulation. Fixation structures may be suture holes, or may protrude from the distal lead body to engage tissue at the implant site. Examples of protruding fixation structures include tines or barbs. Further, protruding fixation structures may be passively or actively deployable, and may include an expandable structure formed of, for example, hydrogel or nitinol.

In some embodiments, the lead body may comprise a paddle-shape, e.g., the lead may be a paddle lead, having one or more fixation structures for securing the lead to tissue to prevent migration. Typically, paddle leads are implanted in an epidural space or other substantially confined region. In contrast, a paddle lead in accordance with an embodiment of the invention may be implanted in, for example, intra-dermal, deep dermal, or subcutaneous tissue and, consequently, may be more susceptible to migration. A lead with a distal fixation structure according to embodiments of the invention may avoid such migration.

Leads according to the invention may be implanted proximate to and deliver stimulation to tissue and/or nerves for a variety of applications, such as to tissue and/or nerves in various localized regions to alleviate chronic pain, to gastric tissue and/or nerves to alleviate gastroparesis or obesity, to pelvic floor tissue and/or nerves to alleviate incontinence or sexual dysfunction, or other tissue and/or nerves. In some embodiments, leads according to the invention may be used to deliver peripheral neurostimulation. Such neurostimulation may be referred to as "peripheral" in the sense that it is delivered to regions of the body or systems other than central nervous system, i.e., the brain and spinal cord. In addition to the examples described above, peripheral neurostimulation may include peripheral nerve field stimulation (PNFS), which may also be referred to a subcutaneous stimulation.

For PNFS, a lead and associated electrodes are positioned, i.e., implanted, in the tissue of a patient within the region where the patient experiences pain. The electrodes may be implanted within, for example, intra-dermal, deep dermal, or subcutaneous tissues of the patient. When PNFS is delivered, current may spread along paths of lower resistance in multiple layers of tissue proximate to the tissue in which the lead is implanted, e.g., the layers of tissue superior (above) and inferior (below) to the layer of tissue in which the electrodes are implanted. The current may spread in any of numerous directions from the electrodes, but generally spreads parallel to the skin surface. The electric field generated by the electrodes may be controlled or steered by selecting combinations of electrodes from the plurality of electrodes and the polarity of the selected electrodes. Generally, the PNFS current may spread over an area of several centimeters. PNFS is not delivered to a specific nerve.

Depending on the location at which the electrodes are implanted PNFS may be used to treat a variety of types of pain. PNFS may be particularly effective at treating localized types of pain. For example, PNFS may be used to treat pain associated with failed back surgery syndrome (FBBS) or other low back pain, cervical pain, such as in the shoulder or neck, neuralgia or other pain associated with occipital nerves, supra-orbital pain, facial pain, inguinal or other pelvic pain, intercostal or other chest pain, limb pains, phantom limb pain, visceral pain, especially if it is referred to a superficial structure, peroneal pain, or arthritis.

PNFS may ameliorate pain within the region through stimulation of axons or small nerve fibers in the nearby dermal, subcutaneous, or muscular tissues, or the tissues themselves. The stimulation of these axons or fibers may cause orthodromic action potentials that propagate toward the spinal cord, and modulate larger peripheral nerves and dorsal horn cells and/or synapses within the dermatomes that include the pain region, which may reduce pain experienced by a patient in that region. The patient may experiences paresthesia in the dermatome where the electrodes are placed. Consequently, the invention may result in increased stimulation of axons or small nerve fibers in the region in which the lead is implanted and a proportional increase of orthodromic action potentials by delivering PNFS to a larger portion of tissue than would be possible with typical leads, i.e., leads with electrodes positioned on a single surface.

The stimulation of these axons or fibers may also cause antidromic action potentials that propagate toward the skin and modulate sympathetic outflow, which may reduce pain mediated by the sympathetic system, such as with some forms of complex regional pain syndrome. The electrodes that deliver PNFS are not implanted proximate to or aligned with larger, peripheral nerves, to avoid delivery of stimulation to smaller fibers in the peripheral nerves, e.g., A-delta fibers, which may result in a patient experiencing unpleasant sensations.

By way of contrast, PNS involves delivery of stimulation to a specific peripheral nerve via one or more electrodes implanted proximate to or in contact with a peripheral nerve, e.g., a single sided paddle lead implanted underneath the peripheral nerve or cuff electrodes surrounding the peripheral nerve. PNS may be used to deliver stimulation to, for example, the vagal nerves, cranial nerves, trigeminal nerves, ulnar nerves, median nerves, radial nerves, tibial nerves, and the common peroneal nerves. When PNS is delivered to treat pain, one or more electrodes are implanted proximate to or in contact with a specific peripheral nerve that is responsible for the pain sensation.

PNS causes orthodromic action potentials to propagate to the spinal cord via the specific peripheral nerve, diminishing pain. Typically, however, the peripheral nerve, and thus the electrodes implanted proximate to the peripheral nerve, are located "upstream" from the region in which a patient perceives the pain, i.e., closer to the spinal cord than the region of pain. For PNS therapy, it is considered desirable to implant the electrodes upstream from the region in which a patient perceives pain so that the paresthesia resulting from PNS is as widely distributed as the areas innervated by the peripheral nerve.

In some embodiments of the invention, PNFS delivered via a lead according to the invention may be delivered in combination with one or more other types of therapy in order to, for example, address complex or multifocal pain. Other types of therapy that may be delivered in combination with PNFS include spinal cord stimulation (SCS), deep brain stimulation (DBS), cortical stimulation (CS), and one or more drugs. In such embodiments, the other type of therapy delivered in combination with the PNFS, whether electrical stimulation, a drug, or some other therapy, need not be delivered by the same lead or by the same implantable medical device. For example, the other therapy may be delivered by a different lead coupled to the same or a different electrical stimulator, an implantable medical device (IMD) including a reservoir and a dump to deliver a drug, or a non-device modality, such as ingestion of a drug.

PNFS and the one or more other therapies may be delivered simultaneously, or in an interleaved or alternating fashion. For example, when the combined therapies include a plurality of neurostimulation therapies delivered by different leads, the different leads may deliver pulses according to each of the therapies in an alternating or interleaved fashion, e.g., each pulse delivered according to a different one of the therapies. As another example, the different neurostimulation therapies may have different pulse rates, duty cycles or scheduled times for delivery, which may result in alternating delivery of the therapies. Interleaved or alternating delivery of PNFS and one or more other therapies may, for example, reduce the likelihood that neural accommodation or tolerance to a particular drug will impair the efficacy of one or more of the therapies, while still providing therapy at any given time. Further, any or all of the combined therapies may be delivered selectively, e.g., upon request by a user, such as a patient or physician.

In one embodiment, the invention is directed to an implantable medical lead comprising a lead body including a first lead body surface and a second lead body surface, and a plurality of electrodes. A first set of the electrodes is located on the first lead body surface, and a second set of the electrodes is located on the second lead body surface.

In another embodiment, the invention is directed to a method comprising selecting from among a plurality of electrodes of an implantable medical lead, wherein the lead comprises a lead body including a first lead body surface and a second lead body surface, a first set of the electrodes is located on the first lead body surface, and a second set of the electrodes is located on the second lead body surface. The method further comprises delivering electrical stimulation from an implantable medical device to a patient via the selected electrodes.

In another embodiment, the invention is directed to a system comprising an implantable medical lead and an implantable medical device. The lead comprises a lead body including a first lead body surface and a second lead body surface, and a plurality of electrodes. A first set of the electrodes is located on the first lead body surface, and a second set of the electrodes is located on the second lead body surface. The implantable medical device delivers stimulation via a selected combination of the electrodes.

In another embodiment, the invention is directed to an implantable medical lead comprising a lead body that comprises a substantially flat paddle-like shape and one or more electrodes, and a fixation structure located at a distal end of the flat paddle-like shape for securing the lead body to tissue of the patient.

In another embodiment, the invention is directed to an implantable medical lead comprising a lead body that comprises a substantially flat paddle-like shape and one or more electrodes, and a fixation structure that protrudes from the lead body to engage tissue of the patient for securing the lead body to the tissue.

In various embodiments, the invention may provide one or more advantages. For example, a paddle lead or multiple level lead with electrodes on more than one surface may provide a clinician flexibility programming stimulation for a patient. For example, increasing the number and variety of locations of electrodes may result in a greater number and variety of available electrode combinations that can be selected to deliver stimulation. The availability of multiple electrodes in the vicinity of a stimulation site increases the likelihood that an efficacious electrode combination will be identified. Further, beyond the number of electrodes available, the location of the electrodes on different surfaces proximate to different tissues or tissue layers may allow the clinician to selectively program stimulation for delivery to one or more of the tissues or layers, as desired.

Further, locating electrodes on multiple surfaces may facilitate stimulation of a larger region of nerves and/or tissue relative to typical leads, e.g., relative to a paddle lead with electrodes positioned on a single surface. Stimulation of a larger region may more completely alleviate symptoms, such as pain, experienced by the patient Stimulating a large region may be particularly desirable for PNFS, which is not directed to any particular nerve, and generally alleviates pain in and around the tissue region in which the stimulation is delivered, which is a region in which the patient experiences pain.

Further, by including one or more protruding fixation structures on the distal end, proximal end, or both ends, movement of the lead within the body of the patient after implantation may be reduced. Protruding fixation structures may provide a less complicated and quicker method for securing a lead to tissue proximate to the implantation site. For example, forming a suture for securing a lead during, for example, laparoscopic surgery requires a surgeon to manipulate instruments within the confines of cannulas and, while watching remotely through a viewing instrument, pass a needle through tissue and a suture sleeve fixed to the lead and tie knot. Because of this complexity, forming a single suture for fixing a lead may take several minutes and, thus, contribute to a longer surgical time and increased risk of morbidity. In contrast, protruding fixation structures, such as tines, barbs, and expandable or otherwise deployable fixation structures, may provide less complicated and time consuming means for securing the lead to prevent migration.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
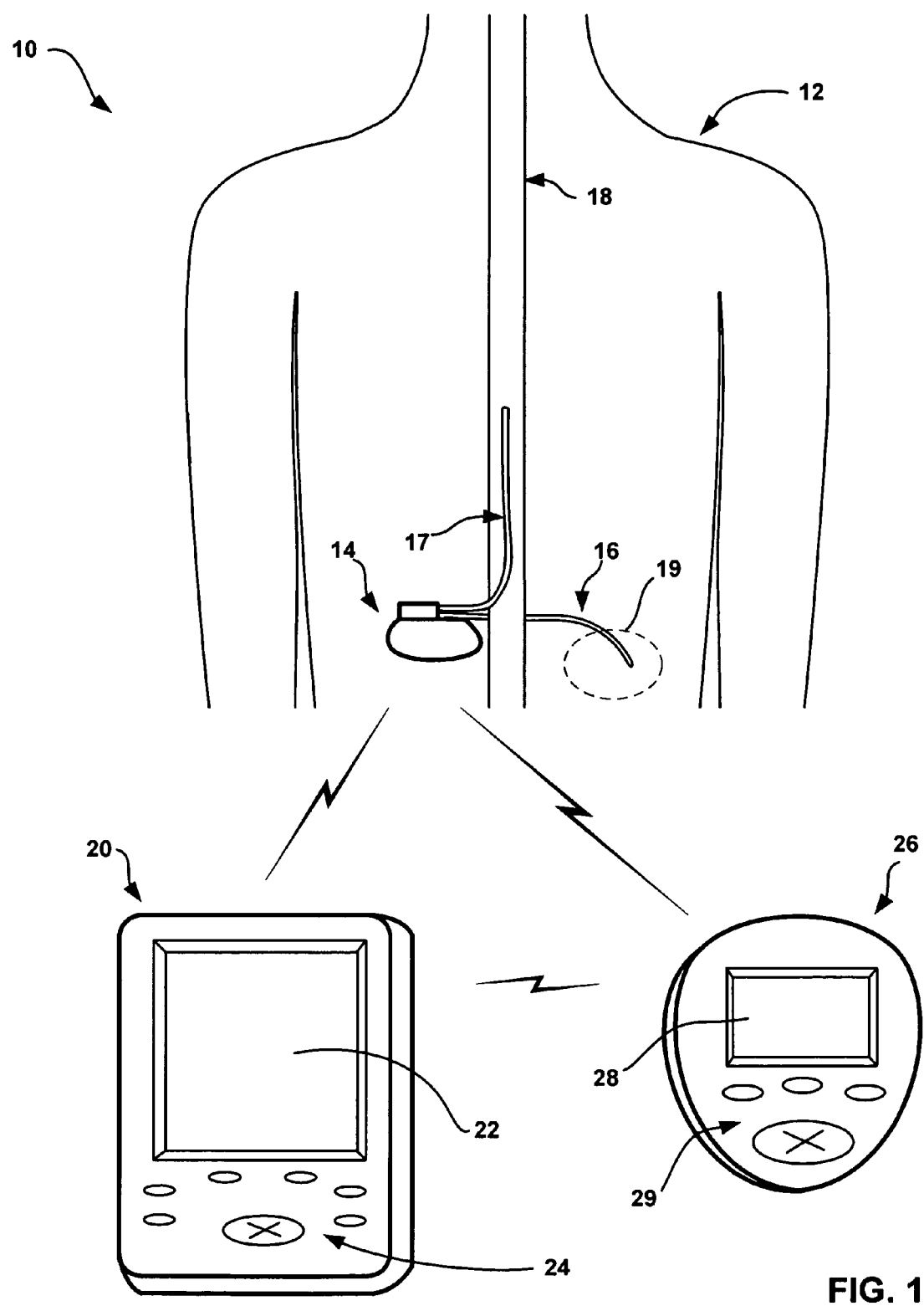
FIG. 1 is a conceptual diagram illustrating an example system for delivering stimulation to a patient.

FIG. 1 is a conceptual diagram illustrating an example system 10 including an implantable medical device (IMD) 14 that delivers stimulation via an implantable medical lead 16. IMD 14 may, for example, deliver peripheral neurostimulation, such as peripheral nerve field stimulation (PNFS), to patient 12 via lead 16. PNFS may also be referred to as subcutaneous stimulation.

As will be described in greater detail below, lead 16 may have a plurality of electrodes located on more than one surface for delivery of stimulation. The location of electrodes on more than one surface of lead 16 may allow IMD 14 to provide stimulation to a larger portion of tissue and/or nerves. By providing stimulation to a larger region, system 10 may more completely alleviate symptoms, such as pain, experienced by patient 12 than would be possible through the delivery of stimulation via a typical lead, e.g., a paddle lead with electrodes on a single surface of the lead. The region where patient 12 experiences pain may be similar to an area that the patient perceives the pain to be located.

Further, IMD 14 may selectively deliver PNFS to different tissues or layers of tissue via the electrodes located on different surfaces of lead 16. Consequently, lead 16 with electrodes located on multiple surfaces may provide a clinician with greater programming flexibility than conventional leads, in that various different tissues or tissue layers may be selected to identify efficacious therapy. For example, lead 16 may be implanted within or between intra-dermal, deep dermal, or subcutaneous tissues of patient 12, and IMD 14 may selectively deliver stimulation to one or more of the layers. These tissues include skin and associated nerves and muscles and associated nerves or muscle fibers.

Lead 16 may comprise a paddle lead or a multiple level lead having a plurality of electrodes, such as pad electrodes, positioned on more than one surface of the lead. In general, a paddle lead comprises a distal lead body with a substantially flat, paddle-like shape. As used herein, the term paddle-like shape refers to distal lead bodies that have, for example, substantially oblong or rectangular cross-sections. FIGS. 2A-2C and FIGS. 3A-3E illustrate example paddle leads having a plurality of electrodes positioned on more than one surface of the paddle lead. A paddle lead having a plurality of electrodes positioned on more than one surface as described in this disclosure is referred to as a dual sided paddle lead. A dual sided paddle lead may be similar to a paddle lead design known in the field of nerve stimulation, but carries electrodes positioned on both sides of the flat insulating body instead of only on one side.

A multiple level lead may have a distal lead body comprising plurality of flat, paddle-shaped lead body levels arranged in substantially parallel planes. Each of the levels includes electrodes located on at least one surface of the level. FIGS. 4A-4E illustrate an exemplary multiple level lead having a plurality of electrodes on more than one surface of the multiple level lead.

The invention described in this disclosure, however, is not limited to lead embodiments that are dual sided paddle leads or a multiple level leads. Rather, the invention described may be implemented as any lead having a distal portion or lead body with more than one surface for carrying electrodes and having electrodes positioned on more than one of the surfaces. In other words, the invention may be embodied by any lead including a distal end or lead body having any of a variety of multi-surfaced shapes and that carries electrodes on more than one of the surfaces.

For example, when lead 16 is implemented as a dual sided paddle lead, electrodes may be positioned on the opposing, parallel, top and bottom surfaces of the dual sided paddle lead. The electrodes positioned on the top surface of the dual sided paddle lead may deliver stimulation to tissue located shallower than the dual sided paddle lead, i.e., tissue located closer to the surface of the skin of patient 12. The electrodes positioned on the bottom surface of the dual sided paddle lead may deliver stimulation to tissue located deeper than the dual sided paddle lead, i.e., tissue located further away from the surface of the skin of patient 12. Consequently, lead 16 may, for example, be implanted in a deep dermal layer of the skin of patient 12, or between the deep-dermal layer and a subcutaneous layer, and may stimulate nerves and/or tissue in one or more of the intra-dermal, deep-dermal and subcutaneous layers of the skin of patient 12. In some embodiments, lead 16 may be a percutaneous lead that is segmented. A segmented lead 16 may include ring electrodes separated circumferentially, such that multiple electrodes are located around the circumference of the lead.

When implemented as a multiple level lead, lead 16 may have electrodes positioned on at least one surface of each level to selectively deliver stimulation to layers of tissue and/or nerves located between adjacent levels. As an example, electrodes may be positioned on adjacent levels such that the electrodes on each level face each other to deliver neurostimulation to tissue located between the two adjacent levels. In other words, electrodes may be positioned on the bottom surface of a first level and on the top surface of a second level that is adjacent and inferior to the first level, i.e., located further away from the surface of the skin of the patient.

As another example, electrodes may be positioned on opposite surfaces of adjacent levels such that the electrodes on each level face away from each other to deliver neurostimulation to different layers of tissue and/or nerves with no overlap. In other words, electrodes may be positioned on the top surface of a first level and on the bottom surface of a second level that is adjacent and inferior to the first level. In this case, the electrodes deliver neurostimulation to a layer of tissue superior to the first level, i.e., closer the surface of the skin of the patient, and to a layer of tissue inferior to the second level. The tissue located between the first and second levels is not stimulated.

In yet another example, electrodes may be positioned on the top and bottom surfaces of each level and may selectively deliver neurostimulation to layers of tissue and/or nerves located between adjacent levels. By positioning electrodes on the top and bottom surfaces of each level, the multiple level lead provides enhanced stimulation programming flexibility. For example, a layer of tissue located between adjacent levels may be stimulated by delivering neurostimulation via electrodes on the bottom surface of the level superior to the layer of tissue, electrodes on the top surface of the level inferior to the layer of tissue, or electrodes on the bottom surface of the level superior to the layer of tissue and electrodes on the top surface of the level inferior to the layer of tissue.

In the example illustrated by FIG. 1, IMD 14 delivers PNFS to a region 19 in which a patient experiences pain. PNFS is delivered to region 19 via the distal end of lead 16. Lead 16 may be implanted within or between, for example, intradermal, deep dermal, or subcutaneous tissues of patient 12 at the region 19 where patient 12 experiences pain, and IMD 14 may selectively deliver PNFS to one or more of these layers. The location of electrodes on multiple surfaces of lead 16 may be particularly advantageous for delivery of PNFS, in that it may allow IMD 14 to deliver PNFS to a greater amount of tissue within region 19 and/or to one or more selected tissues or layers within region 19, which may increase the likelihood that the stimulation will alleviate the pain experienced by patient in region 19.

In the illustrated example, region 19 is an axial region of the lower back of patient 12, but the invention is not limited as such. Rather, lead 16 may be implanted in any region where patient 12 experiences pain, i.e., where patient perceives the pain to be located. For example, lead 16 may extend from IMD 14 to various regions of the back, the back of the head, above the eyebrow, and either over the eye or under the eye, and may be used to treat failed back surgery syndrome (FBBS), cervical pain (shoulder and neck pain), facial pain, headaches supra-orbital pain, inguinal and pelvic pain, chest and intercostal pain, mixed pain (nociceptive and neuropathic), visceral pain, neuralgia, peroneal pain, phantom limb pain, and arthritis.

Further, the invention is not limited to embodiments in which an IMD delivers PNFS via a lead within electrodes on multiple surfaces as described herein. A lead according to the invention may be used for delivery of any type of electrical stimulation. For example, using a lead with electrodes on multiple surfaces, an IMD may deliver any of a variety types of peripheral neurostimulation to tissue and/or nerves for a variety of applications, such as to tissue and/or nerves in various regions to alleviate chronic pain, to gastric tissue and/or nerves to alleviate gastroparesis or obesity, to pelvic floor tissue and/or nerves to alleviate incontinence or sexual dysfunction, and other tissue and/or nerves. As another example, an IMD may deliver peripheral nerve stimulation (PNS) via a lead with electrodes on multiple surfaces according to the invention.

PNFS may be particularly effective at treating localized types of pain. In particular, PNFS may be used to treat a variety of types of pain depending on the location at which lead 16 is implanted. For example, PNFS may be used to treat pain associated with failed back surgery syndrome (FBBS) or other low back pain, cervical pain, such as in the shoulder or neck, neuralgia or other pain associated with occipital nerves, supra-orbital pain, facial pain, inguinal or other pelvic pain, intercostal or other chest pain, limb pains, phantom limb pain, visceral pain, especially if it is referred to a superficial structure, peroneal pain, or arthritis.

When PNFS is delivered, current may spread along paths of lower resistance in multiple layers of tissue proximate to the tissue in which the lead is implanted, i.e., the layers of tissue superior (above) and inferior (below) to the layer of tissue in which the electrodes are implanted. The current may spread in any of numerous directions from the electrodes, but generally spreads parallel to the skin surface. The electric field generated by the electrodes may be controlled or steered by selecting combinations of electrodes from the plurality of electrodes and the polarity of the selected electrodes. Generally, the PNFS current may spread over an area of several centimeters. PNFS is not delivered to any particular nerve.

PNFS may ameliorate pain within the region of implantation by stimulating axons or small nerve fibers in the nearby intra-dermal, deep dermal, subcutaneous, or muscular tissues, or the tissues themselves. The stimulation of these axons or fibers may cause orthodromic action potentials that propagate toward spinal cord 18, and modulate larger peripheral nerves and dorsal horn cells and/or synapses within the dermatomes that include the pain region, which may reduce pain experienced by 12 patient in that region. In other words, patient 12 may experience paresthesia in the dermatome where the lead 16 is implanted. Delivering PNFS via lead 16 may result in increased stimulation of axons or small nerve fibers region 19 and a proportional increase of orthodromic action potentials because lead 16 may deliver PNFS to a larger portion of tissue, i.e., more than one layer of tissue, than would be possible with a typical lead.

The stimulation of these axons or fibers may also cause antidromic action potentials that propagate toward the skin and modulate sympathetic outflow, which may reduce pain mediated by the sympathetic system, such as with some forms of complex regional pain syndrome. When delivering PNFS, lead 16 may be implanted such that its distal end is not proximate to larger, peripheral nerves in order to avoid delivery of stimulation to smaller fibers in the nerve, e.g., A-delta fibers, which may result in a patient experiencing unpleasant sensations.

In contrast to PNFS, peripheral nerve stimulation (PNS) involves delivery of stimulation to a specific peripheral nerve, i.e., a peripheral nerve that is responsible for the pain sensation, via one or more electrodes implanted proximate to or in contact with a peripheral nerve. PNS may be used to deliver stimulation to, for example, the vagal nerves, cranial nerves, trigeminal nerves, ulnar nerves, median nerves, radial nerves, tibial nerves, and the common peroneal nerves.

PNS causes orthodromic action potentials to propagate to the spinal cord via the specific peripheral nerve, diminishing pain. Typically, however, the peripheral nerve, and thus the electrodes implanted proximate to the peripheral nerve, are located "upstream" from the region in which a patient perceives the pain, i.e., closer to the spinal cord than the region of pain. For PNS therapy, it is considered desirable to implant the electrodes upstream from the region in which a patient perceives pain so that the paresthesia resulting from PNS is as widely distributed as the areas innervated by the peripheral nerve.

Typically, a single sided paddle lead is implanted underneath the peripheral nerve or cuff electrodes are implanted surrounding the peripheral nerve to deliver PNS. For delivery of PNS, lead 16 with electrode located on multiple surfaces may be implanted in a similar fashion, i.e., implanted such that a surface of lead 16 carrying one or more electrodes is implanted underneath the peripheral nerve. However, another surface, such as the opposite surface of lead 16 when implemented as a dual sided paddle lead, may also stimulate other nerves and tissue proximate to the peripheral nerve that also contribute to the pain perceived by patient 12. Consequently, delivering PNS via lead 16 may alleviate pain more completely than would be possible using typical leads, e.g., single sided paddle leads or cuff electrodes.

In operation, IMD 14 generates electrical stimulation in accordance with a set of stimulation parameters, which may be referred to as a program. In embodiments in which IMD 14 delivers stimulation in the form of pulses, the stimulation parameters may include voltage or current amplitude, pulse rate, pulse width, and an electrode configuration. An electrode configuration identifies a subset of electrodes selected from the electrodes carried by lead 16 for delivery of stimulation and the polarities of the selected electrodes. In some embodiments, stimulation parameters may differ between electrodes on one surface of lead 16 and electrodes on another surface of the lead. For example, electrodes on separate surfaces of lead 16 may deliver pulses with different pulse widths. Differences in current amplitude, voltage amplitude, pulse frequency, or other parameters may also be possible with lead 16.

In other embodiments, an anode and cathode electrode pair of lead 16 may be located on separate surfaces of the lead. In this case, the electrical current traveling between lead 16 may travel along a side surface of the lead. Lead 16 may be insulated to ensure that current may travel between electrodes on separate surfaces of the lead. In alternative embodiments, one or more electrodes may be located on adjacent surfaces, such as a side surface or edge of lead 16. These electrodes may be in addition or in place of two opposing surfaces. To prevent current from traveling along the side of lead 16, wings or flaps may deploy from lead 16 to prevent a current from traveling in a direction For example, an electrode combination may include all or a subset of electrodes on a first surface of lead 16, such as the top surface of a dual sided paddle lead, and all or a subset of electrodes on a second surface, such as the bottom surface of a dual sided paddle lead. Such an electrode combination enables electrical stimulation to be delivered to tissue located shallower and deeper than lead 16. When coupled to a multiple level lead, IMD 14 may also select electrode combinations to deliver electrical stimulation to corresponding layers of tissue. In any case, the electrode combination may be selected to stimulate tissue and/or nerves in tissue proximate to the implantation site to relieve pain experienced by patient 12.

In some embodiments, IMD 14 delivers stimulation according to a program group including more than one program and, thus, more than one electrode combination. In such embodiments, a first electrode combination may deliver electrical stimulation in accordance with a first set of stimulation parameters and a second electrode combination may deliver electrical stimulation in accordance with a second set of stimulation parameters. The first and second electrode combinations may deliver electrical stimulation to different layers of tissue or nerves at the same time or on a time-interleaved basis. For time-interleaved delivery, stimulation pulses may be delivered in an overlapping or non-overlapping manner, such that stimulation pulses delivered to different selected electrode sets are delivered in respective overlapping or non-overlapping time slots. In any case, the effect resulting from electrical stimulation, i.e., relief from pain, depends on the positions and polarities of the electrodes and the parameters associated with the stimulation pulses. In some embodiments, varying the pulse frequency may allow PNFS to capture target nerve fibers, such as small, medium, or large fibers sensitive to pulse frequency.

A clinician may test all or at least a portion of the possible electrode combinations of electrodes in order to identify an effective combination of electrodes and their polarities. Efficacy may be judged in terms of therapeutic effect in relieving pain experienced by patient 12 and in terms of the absence of undesirable side effects. Efficacy also may be judged in terms of power efficiency provided by the selected electrode combination, particularly in light of the limited battery resources that may be available within IMD 14.

As shown in FIG. 1, system 10 may also include another implantable medical lead 17, and IMD 14 delivers another type of stimulation therapy to patient 12 in combination with the stimulation therapy, e.g., PNFS, delivered via lead 16. Through delivery of a combination therapy, system 10 may be able to more completely address complex symptomology, such as complex or multifocal pain, than would be possible through delivery each of the therapies individually. In addition, the combination of multiple types of therapy may reduce the likelihood that neural accommodation or plasticity will impair the perceived effectiveness of any of the therapies.

However, the invention is not limited to embodiments that provide a combination of therapies. In some embodiments, IMD 14 may deliver a single type of stimulation therapy via one or more leads with electrodes on multiple surfaces. For example, in some embodiments, IMD 14 may deliver PNFS to any one or more of the regions discussed above via one or more leads 16 with distal ends implanted in those regions.

In the illustrated example of FIG. 1, lead 17 extends to spinal cord 18, and IMD 14 delivers spinal cord stimulation (SCS) via one or more electrodes (not shown) carried by lead 17. The electrodes may be implanted in, for example, an epidural space or proximal to dorsal root entry zone of patient 12. In some embodiments, the electrodes are located within a region defined by vertebral levels T7-L1. For example, lead 17 may be implanted in the epidural space near vertebral levels T8-T10 to treat axial back pain, over the dorsal roots of L3-S1, over the dorsal columns at vertebral levels T10-L1 to treat pain in the ankle or foot, or near vertebral levels T9-T11 give paresthesia to the entire thigh. SCS may be most effective at treating neuropathic pain, such as neuropathy or radiculopathy that involves a substantial portion of one limb and more than one dermatome.

However, the invention is not limited to embodiments in which lead 17 extends to spinal cord 18, or IMD 14 delivers SCS. In other embodiments, for example, lead 17 may extend to a location closely proximate to a particular peripheral nerve responsible for causing patient 12 to experience pain, and IMD 14 may deliver PNS to the peripheral nerve. In still other embodiments, lead 17 may extend to the brain of patient 12 (not shown) via a hole formed in the cranium of the patient, and IMD 14 may deliver DBS or CS. For DBS, electrodes may be implanted within the brain, and for CS, electrodes may be implanted within or proximate to the brain.

Further, the invention is not limited to embodiments in which the other therapy treats pain or is a type of neurostimulation. In some embodiments, for example, a drug may be delivered in combination with the PNFS or other stimulation delivered by lead 16. A single implantable medical device (IMD) may include circuitry to deliver stimulation via lead 16, and a reservoir and pump to deliver the drug. Alternatively, systems that deliver a drug in combination with stimulation delivered via lead 16 may include a separate implantable or external pump, or a transdermal delivery mechanism, such as a patch. In some embodiments, a drug is taken orally by a patient in combination with delivery of PNFS.

A combination of therapies may be delivered by any number of devices or other modalities, via any number of leads, catheters, or the like. In some embodiments, multiple IMDs may communicate to coordinate delivery of a combination therapy, e.g., via radio-frequency wireless communication or body conduction.

System 10 may deliver a combination therapy, including delivery of stimulation such as PNFS via lead 16, in order to address complex or multifocal pain. Many cases of axial pain are complex, i.e., both neuropathic (prior nerve injury) and nociceptive (ongoing stimuli). Additionally, a patient may have pain localized in a small area that is uniformly unresponsive to SCS or PNS. For example, a patient may experience arthritis pain in part of one limb, trunkal pain of post-herpetic neuralgia (PHN), or limb pain from advanced complex regional pain syndrome (CRPS) after trophic changes are irreversible. Current advanced pain management therapies for neuropathic pain, nociceptive pain, and/or axial pain may have effective treatment for a portion of the pain experienced by patient 12, but do not always relieve a patient from their pain entirely. For example, when delivering only SCS, the patient may still experience nociceptive pain since SCS only treats neuropathic pain.

As an example, patients with failed back surgery syndrome (FBBS) often have both axial pain due to pressure, instability, inflammation and nerve damage near the vertebra, and radiculopathy down one or both legs due to prior damage to nerve roots. Typically, only one modality of therapy, such as stimulation or drugs, is used since each modality has an implanted device that has its own advantages and disadvantages. Consequently, a physician may pick the modality that treats the worst pain even though pain location, nature, intensity, and other pain characteristics may change over time.

For example, SCS delivered via a set of electrodes at vertebral levels T8-T10 may be used to treat axial pain and, in some cases, may even give paresthesia into parts or all of the legs. However, such SCS stimulation often cannot give paresthesia into the feet, since fibers ascending in the dorsal columns from feet are small and possibly deep at the mid-thoracic levels. Thus, another set of electrodes may be implanted over the dorsal roots at L3-S1, or over the vertebral levels T10-L1. However, the relief of axial pain may fade over a period of time because even with delivering stimulation to different areas of the spinal cord the patient may focus on the remaining axial pain and may be relatively dissatisfied.

Furthermore, even if a patient has only axial back pain, or pain in a localized region of the trunk, using only one modality of stimulation may not be sufficient to relieve a substantial amount of the pain experienced by the patient. Moreover, SCS alone has a limitation for pain in the upper arms and neck since leads placed in the epidural space at the upper thoracic and cervical vertebral levels often move significantly relative to the spinal cord. Consequently, the level of paresthesia can change dramatically thereby preventing sleep or use during normal movements.

In addition, the nervous system has many parallel paths that communicate sensations, including pain, to the brain. Examples of such paths include the lateral spinothalamic paths, the dorsal columns (especially for visceral pain), the spinoreticular paths (for alerting), and spinocerebellar paths. When one of the paths is interrupted to diminish pain, the pain often eventually returns via another pathway.

PNFS or other stimulation delivered via lead 16 can be used in combination with other therapies to affect different brain and spinal areas separately. In particular, delivering PNFS in combination with one or more other therapies may provide a synergistic effect by targeting different portions of the neural "circuit" thereby reducing the likelihood that neural accommodation will reduce the efficacy of one of the therapies. Thus, delivering PNFS in combination with one or more other therapies may more completely address complex pain than would be possible through delivery of either PNFS or the other therapies alone.

IMD 14 may deliver combined therapies simultaneously, or in an interleaved or alternating fashion. For example, when the combined therapies include a plurality of stimulation therapies, IMD 14 may deliver electrical pulses according to each of the therapies via respective ones of leads 16, 17 in an alternating or interleaved fashion, e.g., each pulse delivered according to a different one of the therapies. Consequently, the delivery of each therapy can be optimized at each site. As another example, the different electrical stimulation therapies may have different pulse rates, duty cycles, or scheduled times for delivery, which may result in alternating delivery of therapies. Thus, electrical pulses can be interleaved so as to deliver the same frequency of electrical pulses to respective sites, but with varying amplitudes or pulse widths.

Alternatively, a packet of pulses may be delivered to a PNFS site, such as region 19 via lead 16, with or without ramping of amplitude from start to finish, followed by delivering another packet of pulses to, for example, a SCS site via lead 17. Interleaved or alternating delivery of stimulation via lead 16 and one or more other electrical stimulation therapies via lead 17 may, for example, reduce the likelihood that neural accommodation or plasticity will impair the efficacy of one or more of the therapies, while still providing therapy at any given time. In particular, avoiding constant stimulation at a site, such as region 19 or otherwise, may prevent neural accommodation that would reduce the efficacy of one or more of the therapies.

Interleaved or alternating delivery of PNFS or other stimulation via lead 16 and one or more other electrical stimulation therapies may also prevent overuse or depletion of transmitters, such as GABA-B, that are major inhibitory transmitters released in the dorsal horn when electrical stimulation produces pain relief. Further any or all of the combined therapies may be delivered selectively, e.g. upon request by a user, such as a physician or a patient. In other words, system 10 may provide multiple therapies that may be selected by a user, e.g., as the pain experienced dictates, but need not deliver a plurality of therapies at all times.

System 10 includes a clinician programmer 20 for programming stimulation delivered to patient 12 via lead 16, such as PNFS, and, in some embodiments, another type of therapy, which may be stimulation delivered via lead 17 as illustrated. Clinician programmer 20 may, as shown in FIG. 1, be a handheld computing device. Clinician programmer 20 includes a display 22, such as a LCD or LED display, to display information relating to neurostimulation delivered via lead 16 and one or more of the other therapies delivered via lead 17 to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

A clinician (not shown) may use clinician programmer 20 to program stimulation, such as PNFS, delivered via lead 16. In some embodiments, a clinician may also use clinician programmer 20 to program another type of therapy delivered in combination with the stimulation delivered via lead 16. For example, the clinician may use clinician programmer 20 to select values for therapy parameters, such as pulse amplitude, pulse width, pulse rate, electrode polarity and duty cycle, for both the stimulation delivered via lead 16 and another type of stimulation delivered via lead 17. As another example, in embodiments in which the combination therapy additionally or alternatively includes delivery of a therapeutic agent, the stimulation parameters may include an infusion rate, concentration, ratio (if two or more drugs are delivered), and duty cycle are examples of therapy parameters for drug delivery.

IMD 14 may deliver the therapies of a combination according to respective programs, each program including respective values for each of a plurality of such therapy parameters. Further, IMD 14 may deliver the therapies in accordance with a program group. A program group may contain one or more programs. A program group may include, for example, one or more PNFS programs to control the delivery of stimulation via lead 16, and one or more programs for the other therapy, such as one or more SCS programs to control the delivery of stimulation via lead 17. IMD 14 may deliver stimulation pulses according to a program group by "interleaving" the pulses for each program, e.g., delivering each successive pulse according to a different one of the programs of the program group.

To create a programs and program groups the clinician may select existing or predefined programs, or specify programs by selecting therapy parameter values. The clinician may test the selected or specified programs on patient 12, and receive feedback from patient 12. Highly rated programs may be provided to IMD 14 or a patient programmer, individually or as program groups, and used by IMD 14 to control delivery of stimulation. The clinician may identify preferred programs for the stimulation delivered via lead 16 and one or more other therapies delivered via lead 17 separately, or through delivery of the therapies together.

System 10 also includes a patient programmer 26, which also may, as shown in FIG. 1, be a handheld computing device. Patient programmer 26 may also include a display 28 and a keypad 29, to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus or mouse.

Patient 12 may use patient programmer 26 to control the delivery of stimulation, e.g., PNFS, by IMD 14 via lead 16 and the at least one other therapy via lead 17. Patient 12 may use patient programmer 26 to activate or deactivate any of a combination of therapies, and may use patient programmer 26 to select the programs or program group that will be used by IMD 14 to deliver the combination of therapies. Further, patient 12 may use patient programmer 26 to make adjustments to programs or program groups. Additionally, the clinician or patient 12 may use programmers 20, 26 to create or adjust schedules for delivery of the different therapies of the combination. Such schedules may provide for alternating delivery of the therapies.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using any telemetry techniques known in the art. Such techniques may include low frequency or radiofrequency (RF) telemetry, but other techniques are also contemplated. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

Figure 2A:
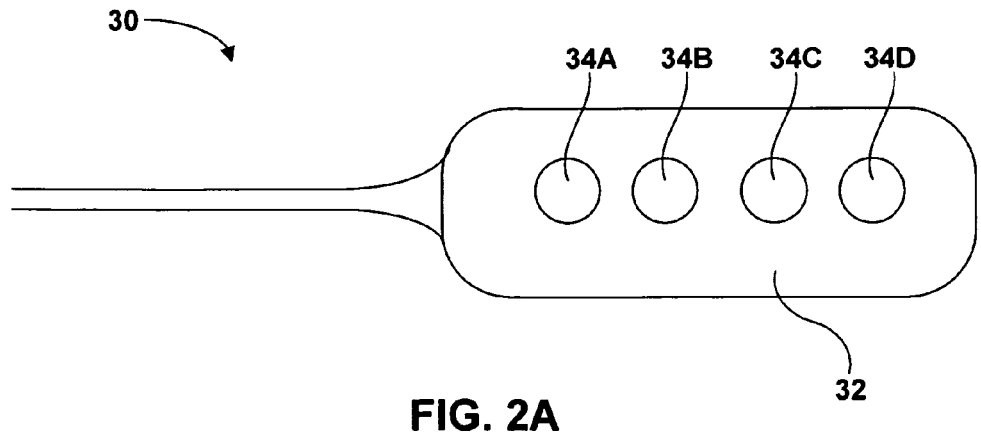
FIGS. 2A-2C are schematic diagrams illustrating a top view and side views of example implantable medical leads having a plurality of electrodes located on more than one surface of the lead.
Figure 2B:
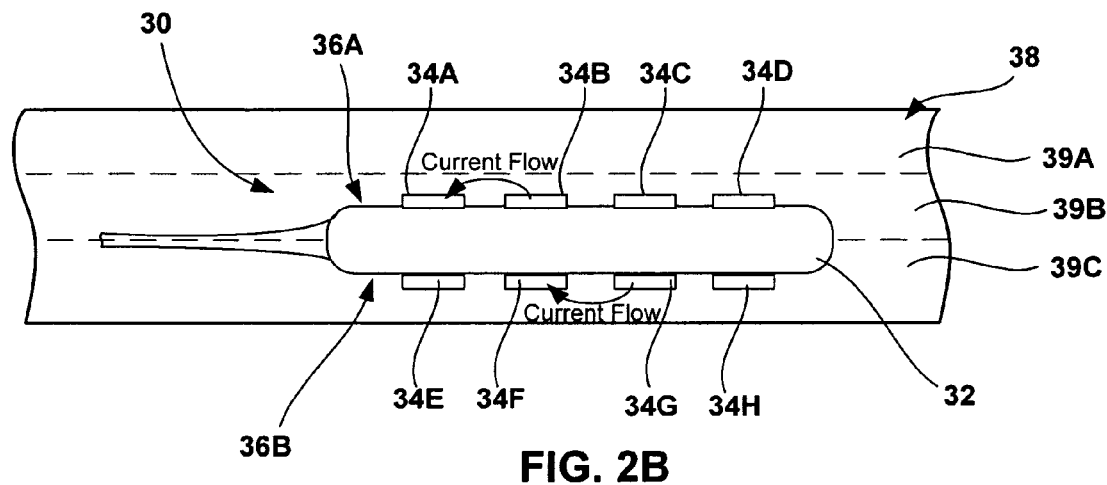
Figure 2C:
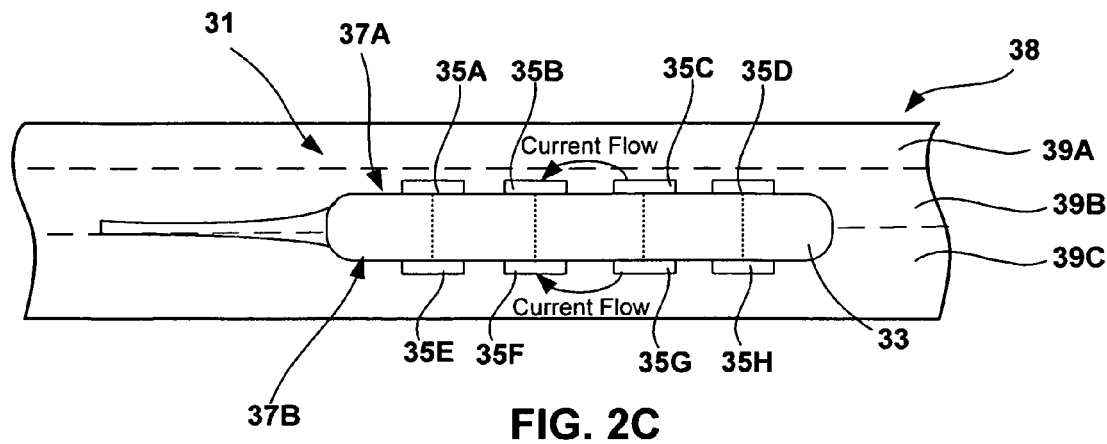

FIGS. 2A-2C are schematic diagrams illustrating a top view and side views of example leads with electrodes on multiple surfaces. More particularly, FIGS. 2A-2C illustrate examples of dual sided paddle leads. As discussed above, the invention is not limited to paddle leads, and may include any lead with electrodes on multiple surfaces.

FIGS. 2A and 2B are schematic diagrams illustrating a top and a side view, respectively, of dual sided paddle lead 30. FIG. 2B illustrates lead 30 implanted within tissue 38 of patient 12. Dual sided paddle lead 30 may be implanted in intra-dermal, deep dermal, or subcutaneous tissue of the patient.

Dual sided paddle lead 30 includes a lead body 32 carrying electrodes 34A-H (collectively referred to as "electrodes 34") located at its distal end. Lead body 32 may be designed similar to a paddle lead design known in the field of nerve stimulation, but, as shown, carries electrodes positioned on first and second surfaces 36A and 36B (collectively "surfaces 36"), e.g., the illustrated opposing, substantially parallel, top and bottom surfaces, instead of only on one surface. Lead body 32 has a substantially flat, paddle-like shape, e.g., has a substantially oblong or rectangular cross-sectional shape.

As shown in FIG. 2B, electrodes 34A-D are positioned on top surface 36A of lead body 32 and electrodes 34E-H are positioned on the bottom surface 36B of lead body 32. Electrodes 34A-H (collectively "electrodes 34") may extent above surfaces 36, may be recessed relative to the surfaces 36, or may be co-planar with the surfaces. Electrodes 34 may be electrically insulated from each other.

In the illustrated example of FIGS. 2A and 2B, dual sided paddle lead 30 includes eight electrodes, i.e., electrodes 34, positioned on the top and bottom surfaces of lead body 32 for purposes of illustration. However, dual sided paddle lead 30 may include a lesser or greater number of electrodes. A dual sided paddle lead having numerous electrodes may be particularly advantageous because the number of electrode possible combinations increases with the number of electrodes carried by the lead. In other words, providing a large number of electrode combinations increases the likelihood of discovering an electrode combination that achieves a high clinical efficacy with minimal side effects and favorable power consumption characteristics.

Electrodes 34 are arranged in a linear array along substantially the entire length of the top and bottom surfaces 36 of lead body 32. However, the invention is not limited as such. Rather, electrodes 34 may also be arranged in a two-dimensional array or any other regularly or irregularly spaced pattern, and may be distributed in discrete groups or "clusters," or be distributed substantially evenly over substantially the entirety of surfaces 36. FIGS. 3C-E illustrate various configurations of electrodes for dual sided paddle leads. In any case, each of electrodes 34 may be electrically coupled to an IMD (not shown), such as IMD 14 of FIG. 1, via a separate electrical conductor (not shown). The electrical conductors may reside in lead 30, where they may be electrically insulated protected from body fluids.

The IMD may select one or more of electrodes 34 for electrode combinations to deliver stimulation to a patient as described in FIG. 1. With respect to FIG. 2B, electrodes 34 carried by dual sided paddle lead 30 deliver neurostimulation to tissue 38. In particular, electrodes 34A-D may deliver neurostimulation to tissue 39A located shallower than lead 30 and electrodes 34E-H may deliver neurostimulation therapy to tissue 39C located deeper than lead 30. For example, dual sided paddle lead 30 may be implanted between deep dermal tissue layer 39B and subcutaneous tissue layer 39C, and may stimulate nerves and/or tissue in both deep dermal tissue layer 39B and subcutaneous tissue layer 39C, as well as tissue within inter-dermal tissue layer 39A. However, the invention is not limited as such. Rather, dual sided paddle lead 30 may be implanted within or between any of the intra-dermal, deep dermal, or subcutaneous tissue, or within any tissue or tissue layer of a patient. The height of dual sided paddle lead 30, i.e., the distance between electrodes 34A-D and electrodes 34E-H, may be varied or selected depending on various design parameters, such as the tissues or layers for which stimulation is desired, as well as the anticipated proximity of lead 30 to such tissues or layers. Further, the depth of different layers of tissue of the patient may vary depending on the anatomy of the patient, e.g., layers of tissue of an obese patient may be thicker than those of a slender patient.

In other embodiments in which lead body 32 is implanted within a particular tissue layer, such as deep dermal layer 39B, the thickness of lead 30 may also affect the degree of neurostimulation delivered to that layer. For example, if the thickness of lead 30 is sufficiently large, tissue 39B may not be substantially stimulated. However, the thickness of lead 30 may be sufficiently small that tissue 39B is stimulated to some degree. As a result, dual sided paddle lead 30 may be configured to stimulate substantially distinct layers of tissue.

Further, IMD 14 may selectively deliver stimulation via a variety of combinations of electrodes 34. Based on the electrodes within the combination and their polarity, as well as other stimulation parameters such as amplitude, IMD 14 may generate a current field via the selected electrodes that stimulates desired tissues or layers. IMD 14 may deliver stimulation via combinations of electrodes 34 on a single surface 36 to stimulate one or more layers of tissue proximate to that surface, or combinations that include electrodes 34 on both surfaces 36. Further, IMD 14 may simultaneously or alternatingly deliver stimulation via combinations of electrodes 34 from respective surfaces 36, to simultaneously or alternatingly stimulate layers above or below lead body 32.

In the illustrated example of FIG. 2B, electrodes 34A and 34B may be selected as the first electrode combination and electrodes 34F and 34G may be selected as the second electrode combination. Accordingly, a current flow is shown between electrodes 34A and 34B and electrodes 34F and 34G in FIG. 2. In such embodiments, the first electrode combination may deliver electrical stimulation in accordance with a first set of stimulation parameters and the second electrode combination may deliver electrical stimulation in accordance with a second set of stimulation parameters. For time-interleaved delivery, stimulation pulses may be delivered in an overlapping or non-overlapping manner, such that stimulation pulses delivered to different selected electrode sets are delivered in respective overlapping or non-overlapping time slots. In any case, the effect resulting from electrical stimulation, i.e., relief from pain or paresthesia, depends on the positions and polarities of the electrodes and the parameters associated with the stimulation pulses.

FIG. 2C is a schematic diagram illustrating a side view of another example dual sided paddle lead 31 implanted within tissue 38 of patient 12. Similar to dual sided paddle lead 30, dual sided paddle lead 31 includes a lead body 33 located at its distal end. Like lead 30, dual sided paddle lead 31 may also include electrodes 35A-D located on a first lead body surface 37A, and electrodes 35E-H located on a second lead body surface 37B.

However, in contrast to dual sided paddle lead 30, electrodes 35A-D are electrically coupled to corresponding ones of electrodes 35E-H, as illustrated by the dotted line in FIG. 2C. Any number of electrodes 35A-H on either of surfaces 37A and 37B may be electrically coupled such that they will deliver stimulation at the same time and with the same electrical characteristics, e.g., according to the same program. In the illustrated example, current flows from coupled electrodes 35C and 35G, which are act as cathodes on respective ones of surfaces 37A and 37B, to coupled electrodes 35B to 35F, which act as anodes.

Such coupling may reduce the programming flexibility of lead 31 by providing fewer different combinations of electrodes 35A-H that may be selected by a clinician. Further, where electrodes 35A-H on different surfaces 37A and 37B are electrically coupled, the ability of IMD 14 to deliver stimulation via either surface to particular layers or tissues may be limited or eliminated. However, a lead with fewer conductors may be more cost effective to manufacture, more flexible, and less prone to failure due to, for example, fracturing or degradation of the conductors. Further, in some embodiments, simultaneous delivery of stimulation to a large tissue region may be preferred over selectability of tissues or layers.

Figure 3A:
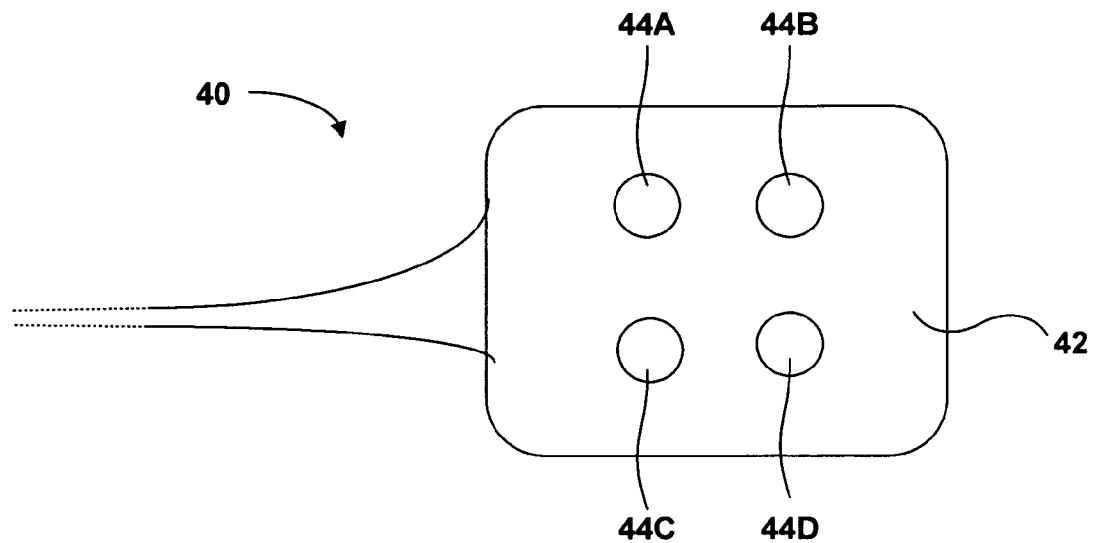
FIGS. 3A-3E are schematic diagrams illustrating top views of other example implantable medical leads having a plurality of electrodes located on more than one surface of the lead.
Figure 3B:
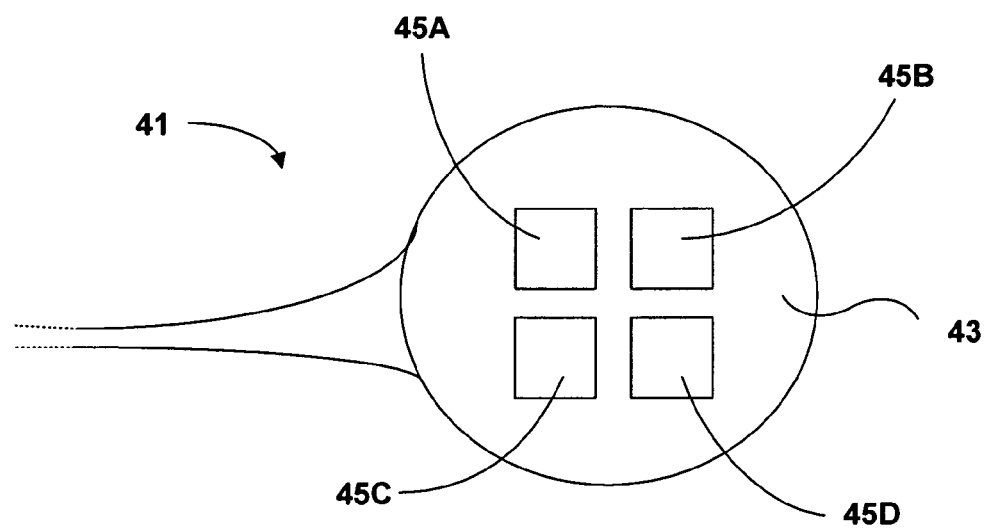
Figure 3C:
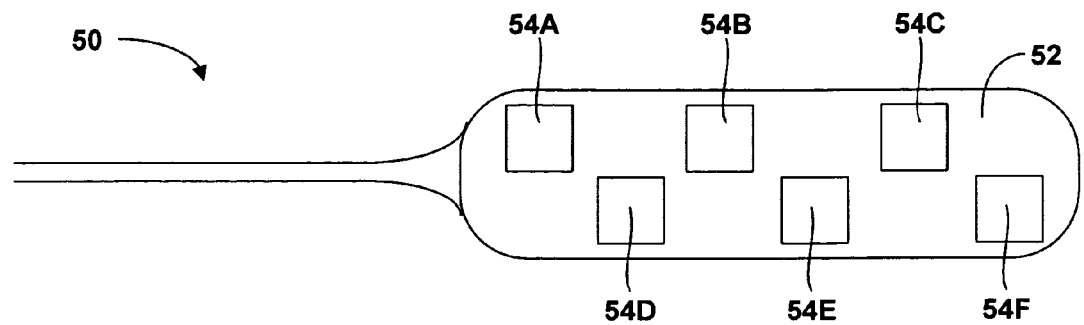
Figure 3D:
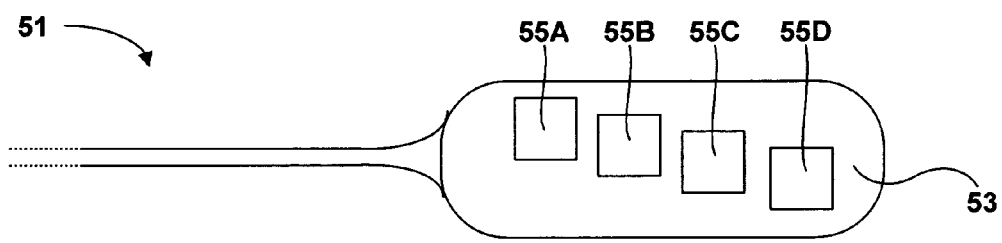
Figure 3E:
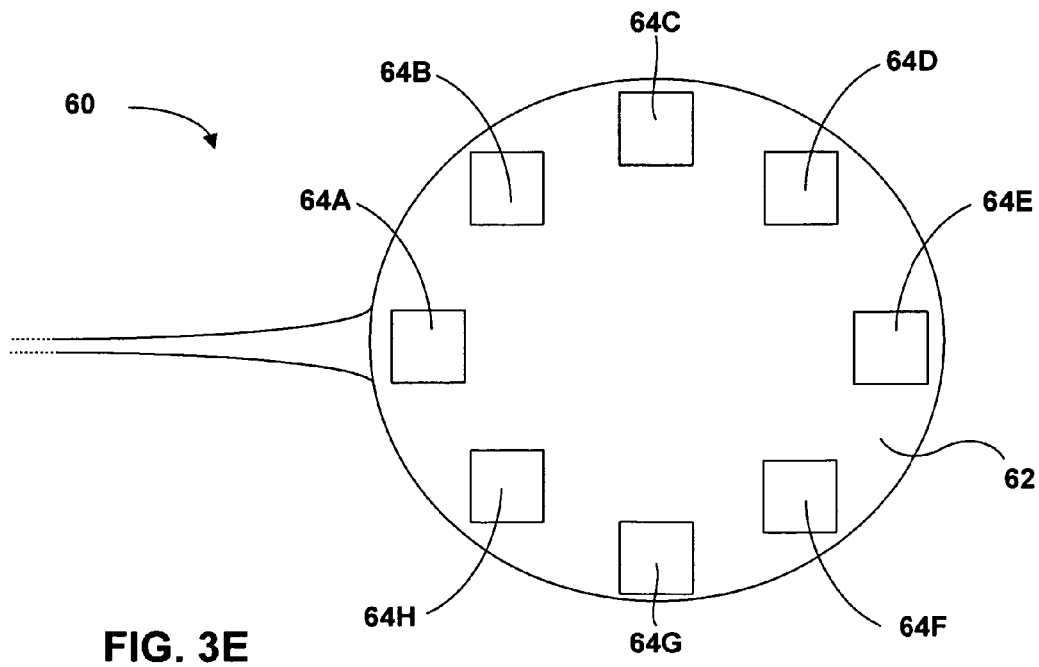

FIGS. 3A-3E are schematic diagrams illustrating top views of example dual sided paddle leads. In particular, FIG. 3A is a top view of dual sided paddle lead 40 having a circularly shaped lead body 42 and FIG. 3B is a top view of dual sided paddle lead 41 having a square shaped lead body 43. The circular shape of lead body 42 may require substantial dissection for implantation within patient 12, but may provide a form factor that best covers the patient's perceived region of pain. In contrast, the square or rectangular shape of lead body 43 be characterized by a substantially smaller width than lead body 42 and, thus, may reduce the amount of tissue damage caused during implantation. The illustrated surfaces of lead bodies 42 and 43 respectively include electrodes 44A-D and electrodes 45A-D. At least one other surface of lead bodies 42 and 42, such as an opposing or bottom surface not shown in FIGS. 3A and 3B, includes additional electrodes.

FIGS. 3A and 3B are merely exemplary and should not be considered limiting of the invention as broadly described in this disclosure. For example, a dual sided paddle lead as described in this disclosure may have a leady body that is circular, rectangular, square, round, oval, or any other uniform or non-uniform shape. Accordingly, the lead body may be shaped to match the patient's perceived region of pain, to reduce the amount of tissue damage cause during implantation, or achieve a tradeoff of these design parameters. Further, lead body shapes illustrated in FIGS. 3A and 3B are not limited to dual sided paddle leads. Rather, separate lead body levels of a multiple level lead, as will be described below, may have the illustrated shapes.

FIGS. 3C-E are schematic diagrams illustrating top views of other example dual sided paddle leads with various configurations of electrodes. However, the configurations of electrodes illustrated in FIGS. 3C-E are not limited to dual sided paddle leads. Rather, the configurations of electrodes illustrated in FIGS. 3C-E may also be used with multiple level leads described in this disclosure.

FIG. 3C is a top view of a dual sided paddle lead 50 having an elongated lead body 52 located at the distal end of lead extension 56. Lead body 52 carries a two dimensional array of electrodes 54A-F (collectively referred to as "electrodes 54") on its top surface. A two-dimensional array generally refers to an ordering of electrodes along at least two different lines, e.g., as rows and columns. As shown in FIG. 3C, electrodes 54 are arranged in two evenly spaced rows that are staggered relative to each other. Alternatively, electrodes may be positioned irregular intervals within a line or at positions that do not represent an ordered pattern. In some embodiments, a two-dimensional array of electrodes may comprise electrodes arranged in three or more rows.

FIG. 3D is a top view of a dual sided paddle lead 51 having an elongated lead body 53 located at the distal end of lead extension 57. Lead body 53 carries a linear array of electrodes 55A-D (collectively referred to as "electrodes 55") on its top surface. A linear array generally refers to an ordering of electrodes along a common line. In the illustrated example of FIG. 3D, electrodes 55 are arranged along the longitudinal axis of lead body 53 at regular intervals and are offset from each other rather than being in line with the longitudinal axis.

FIG. 3E is a top view of a dual sided paddle lead 60 having a circular shaped lead body 62 located at the distal end of lead extension 66. Lead body 62 carries electrodes 64A-H (collectively referred to as "electrodes 64") on its top surface. Electrodes 64 are arranged in an ordered pattern about the circumference of lead body 62 with regular spacing. The number of electrodes shown in FIG. 3E is merely exemplary. Any number of electrodes may be arranged in an ordered pattern or, alternatively, at positions that do not represent an ordered pattern. In any case, the number and pattern of electrodes may be selected based on the patient's perceived region of pain.

FIGS. 4A-D are schematic diagrams illustrating side views of example multiple level leads implanted within tissue 100. Each of FIGS. 4A-D illustrates a multiple level lead with electrodes positioned on various surfaces to selectively deliver stimulation to layers of tissue located proximate to or between adjacent levels of the lead. As previously described in this disclosure, a multiple level lead may be implanted within intra-dermal, deep dermal, or subcutaneous tissue of a patient and includes one or more electrodes positioned on at least one surface of each level of the lead. In other embodiments, a lower level of the lead may be implanted within a muscle tissue or under a muscle tissue.

Each of the multiple level leads illustrated in FIGS. 4A-D include a lead body with two lead body levels, i.e., an upper level and a lower level. Each of the lead body levels may have a substantially flat, paddle-like shape, as described above with reference to paddle leads and FIGS. 2A-C. However, the invention is not so limited. Rather, a multiple level lead may include any number of lead body levels with any shape. In the interest of brevity, FIGS. 4A-D illustrate the various configurations for a multiple level lead having two levels. A multiple level lead having more than two levels follows from the description provided in this disclosure. Accordingly, FIGS. 4A-D are merely exemplary and should not be considered limiting of the invention as broadly described in this disclosure. Fro example, the lead body may be substantially cylindrical.

Figure 4A:
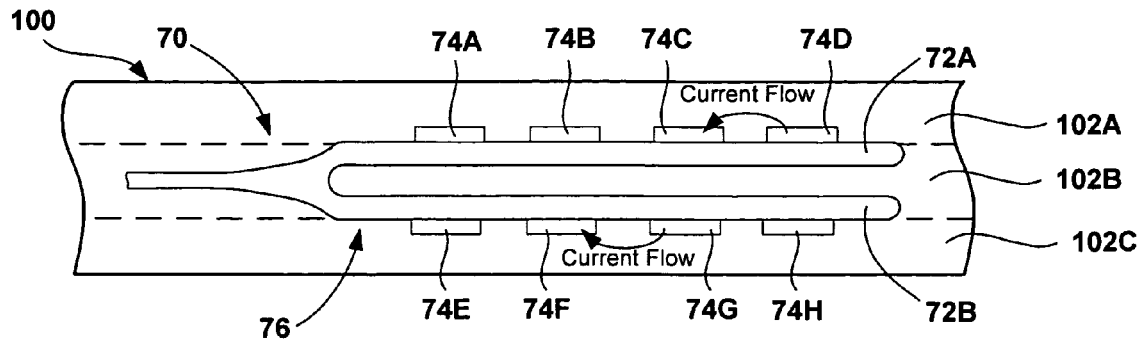
FIGS. 4A-4D are schematic diagrams illustrating side views of other example implantable medical leads with electrodes positioned on various surfaces.

FIG. 4A illustrates multiple level lead 70 implanted within tissue 100 of patient 12. Multiple level lead 70 includes a lead body 76 at its distal end comprising an upper lead body level 72A and a lower lead body level 72B (collectively "levels 72"). Upper level 72A may be located closer to the surface of the skin of patient 12 than lower level 72B. Upper level 72A carries electrodes 74A-D on its top surface and lower level 72B carries electrodes 74E-H on its bottom surface. In this manner, multiple level lead 70 carries electrodes 74A-H (collectively "electrodes 74") on opposite surfaces of adjacent levels such that electrodes 74A-D and electrodes 74E-H face away from each other.

In the illustrated example of FIG. 4A multiple level lead 70 includes eight electrodes for the purposes of illustration. However, as previously described with respect to dual sided paddle leads in FIGS. 2A and 2B, multiple level lead 70 may include a lesser or greater number of electrodes. Again, having numerous electrodes may be particularly advantageous because the number of electrode possible combinations increases with the number of electrodes carried by the lead. In other words, providing a large number of electrode combinations increases the likelihood of discovering an electrode combination that achieves a high clinical efficacy with minimal side effects and favorable power consumption characteristics.

Electrodes 74A-D and 74E-H may be arranged in any regular or irregular pattern such as those illustrated in or described with respect to FIGS. 3C-E. For example, electrodes 74A-D and 74E-H may be arranged in the same pattern, such as the two-dimensional array illustrated in FIG. 3C, or may be arranged in different patterns, such as the two-dimensional array illustrated in FIG. 3C and the linear array illustrated in FIG. 3D. In any case, each of electrodes 74A-D and 74E-H may be electrically coupled to an IMD (not shown), such as IMD 14 of FIG. 1, via a separate electrical conductor (not shown) within lead 70.

In operation, the IMD may apply stimulation across selected electrodes of 74A-D and 74E-H to deliver, for example, PNFS to various layers of tissue 100. In particular, one or more of electrodes 74A-D may deliver stimulation to tissue 102A located shallower than upper level 72A and one or more of electrodes 74E-H may deliver stimulation therapy to tissue 102C located deeper than lower level 72B. In one example, multiple level lead 70 may be implanted in deep dermal tissue 102B and may stimulate nerves and/or tissue in both intra-dermal and subcutaneous tissue 102A and 102C, respectively. However, the invention is not limited as such and multiple level lead 70 may be implanted in intra-dermal, deep dermal, or subcutaneous tissue. Regardless of which layer of tissue multiple level lead 70 is implanted, multiple level lead may deliver stimulation to a layer of tissue located shallower than upper level 72A and a layer of tissue located deeper than lower level 72B.

However, the distance between upper level 72A and lower level 72B may be selected based on one or more design parameters. For example, the distance between upper level 72A and lower level 72B may be selected in a similar manner to selecting the thickness of a dual sided paddle lead, as described with respect to dual sided paddle lead 30 in FIGS. 2A and 2B. In particular, the distance may be selected such that upper lead body 72A and lower lead body 72B are implanted within distinct layers of tissue, such as intra-dermal and subcutaneous tissue, respectively. In this case, the distance may vary depending on the anatomy of the patient, e.g., layers of tissue of an obese patient may be thicker than those of a slender patient.

The distance may also affect the degree of stimulation delivered to tissue 102B, i.e., the layer of tissue in which multiple level lead 70 is implanted. For example, if the distance between upper level 72A and lower level 72B is sufficiently large, neurostimulation may only be delivered to tissue 102A and 102C. In other words, tissue 102B may not be substantially stimulated. In contrast, however, the height may be sufficiently small such that tissue 102B is stimulated to some degree.

Again, multiple level lead 70 may deliver stimulation, such as PNFS, to tissue 102A and 102C at the same time or in an alternating or interleaved fashion. For example, a first electrode combination selected from electrodes 74A-D may deliver PNFS to tissue 102A and a second electrode combination selected from electrodes 74E-H may deliver PNFS to tissue 102C. Accordingly, a current flow is shown between electrodes 74C and 74D and electrodes 74F and 74G in FIG. 4A. In such embodiments, the first electrode combination may deliver electrical stimulation in accordance with a first set of stimulation parameters and the second electrode combination may deliver electrical stimulation in accordance with a second set of stimulation parameters. For time-interleaved delivery, stimulation pulses may be delivered in an overlapping or non-overlapping manner, such that stimulation pulses delivered to different selected electrode sets are delivered in respective overlapping or non-overlapping time slots. In any case, the effect resulting from electrical stimulation, i.e., relief from pain or paresthesia, depends on the positions and polarities of the electrodes and the parameters associated with the stimulation pulses.

Figure 4B:
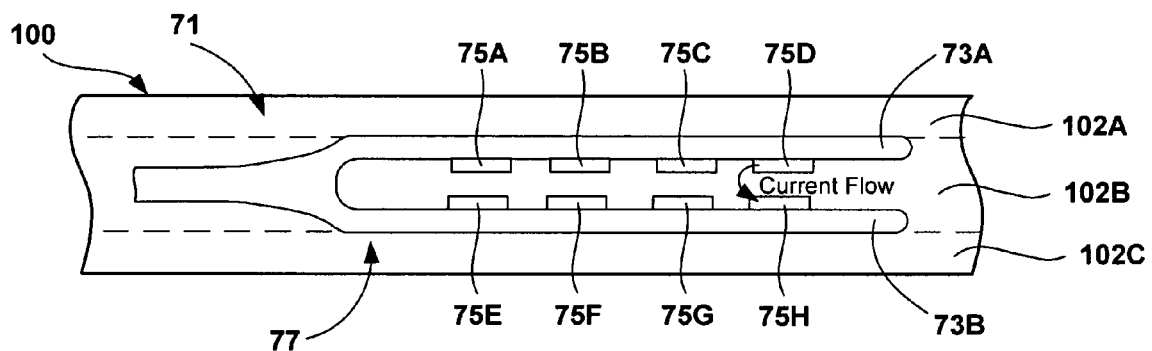

FIG. 4B is a side view illustrating multiple level lead 71 implanted within tissue 100 of patient 12. Similar to multiple level lead 70, multiple level lead 71 includes a lead body 77 with an upper lead body level 73A and a lower lead body level 73B (collectively "levels 73"). However, in contrast to multiple level lead 70, upper level 73A carries electrodes 75A-D on its bottom surface and lower lead body 73B carries electrodes 75E-H on its top surface. As a result, multiple level lead 71 carries electrodes 74A-D and 74E-H on adjacent surfaces of adjacent levels such that electrodes 74A-D and 74E-H face each other.

Consequently, multiple level lead 71 may focus delivery of stimulation to tissue, such as layer 102B, located between adjacent levels 73. With reference to the example illustrated by FIG. 4B, multiple level lead 71 may be able to deliver stimulation to tissue 102B without substantially stimulating tissue 102A located superior to upper level 73A or tissue 102C located inferior to lower level 73B. Upper level 73A and lower level 73B may electrically isolate tissue 102A and 102C from being stimulated by neurostimulation delivered to 102B. Again, tissues 102A, 102B and 102C may correspond to intra-dermal, deep dermal and subcutaneous tissue layers within a region 19, and the IMD may deliver PNSF via lead 71.

In some embodiments, as illustrated by the labeled current flow in FIG. 4B, an IMD may apply electrical stimulation pulses across electrodes 75A-H such that an anode and cathode are not on the same level. However, the invention is not so limited. An IMD may deliver stimulation to tissue between levels 73 via any combination of electrodes 75A-H on one or both of the levels.

Figure 4C:
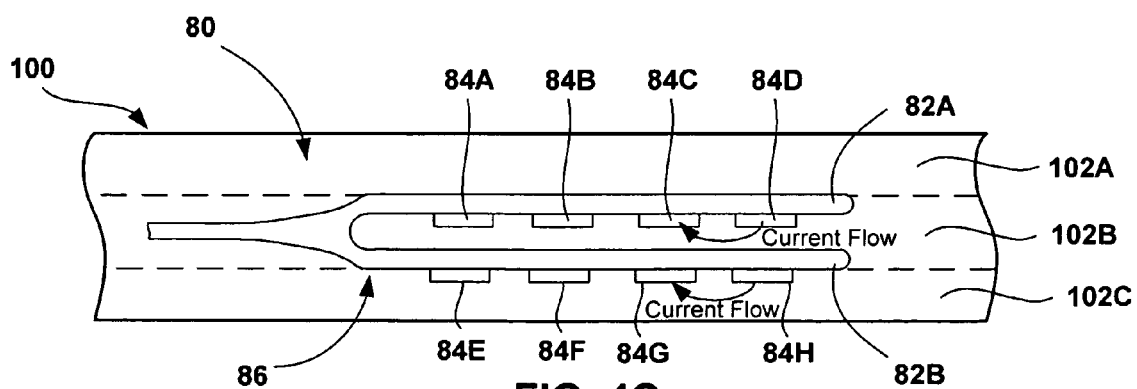

FIG. 4C is a side view illustrating another example multiple level lead 80 implanted within tissue 100 of patient 12. Again, multiple level lead 80 is similar to multiple level leads 70 and 71 with respect to physical structure, i.e., multiple level lead 80 includes a distal lead body 86 with an upper level 82A and a lower level 82B. However, unlike multiple level leads 70 and 71, upper level 82A carries electrodes 84A-D on its bottom surface and lower level 82B carries electrodes 84E-H on its bottom surface. As a result, multiple level lead 80 delivers neurostimulation to tissue 102B located between upper level 82A and lower lead level 82B and tissue 102C located deeper than lower lead body 82B.

In particular, multiple level lead 80 may deliver neurostimulation, such as PNFS, to tissue 102B and 102C without substantially stimulating tissue 102A. In operation, the IMD (not shown) coupled to multiple level lead 80 may apply electrical stimulation pulses across one or more of electrodes 84A-D and one or more of electrodes 84E-H to stimulate tissue 102B and tissue 102C, respectively. In this case, the IMD may select anode and cathode on the same level. As an example, FIG. 4C illustrates a current flow between electrodes 84C and 84D to stimulate tissue 102B and between electrodes 84G and 84H to stimulate tissue 102C. When delivering neurostimulation to tissue 102B and 102C, upper level 82A may substantially electrically isolate tissue 102A from being stimulated by neurostimulation delivered to tissue 102B and tissue 102C.

Figure 4D:
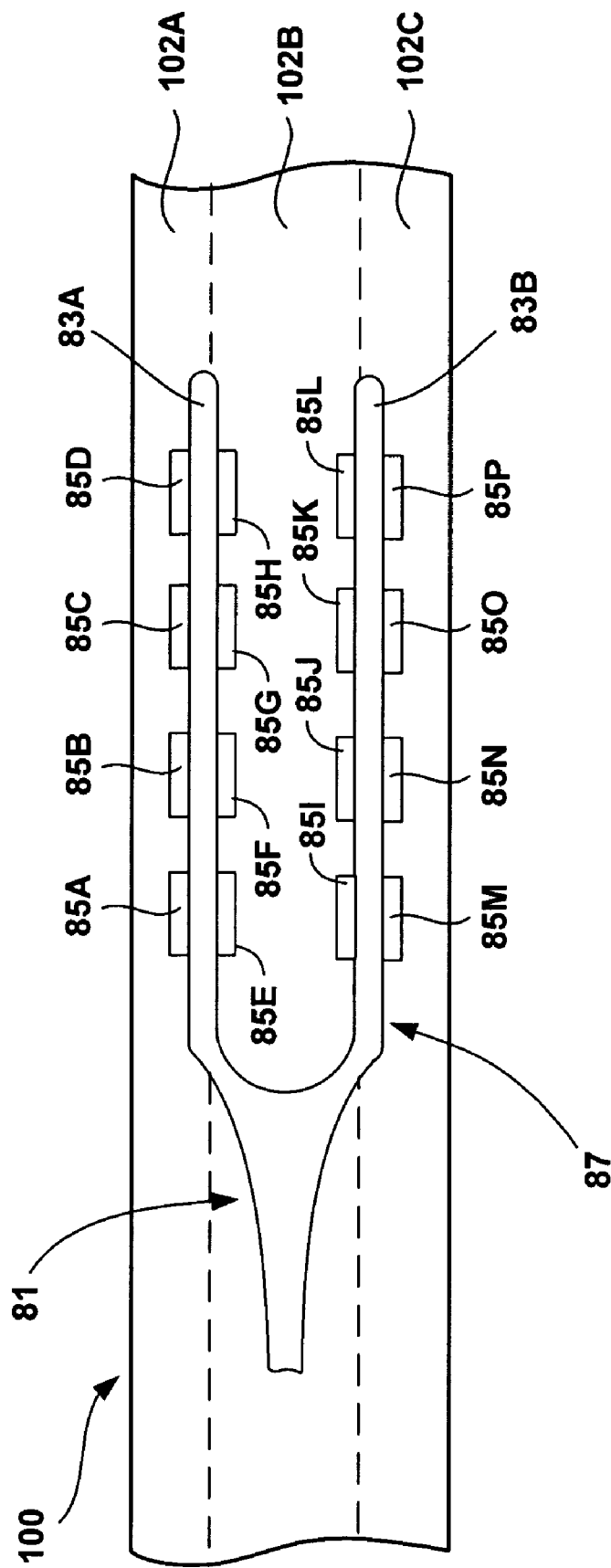

FIG. 4D is a side view illustrating multiple level lead 81 implanted within tissue 100 of patient 12. Multiple level lead 81 is similar to multiple level leads 70, 71, and 80 with respect to physical structure, i.e., multiple level lead 81 includes a distal lead body 81 with an upper level 83A and a lower level 83B. However, unlike multiple level leads 70, 71, and 80, upper level 83A carries electrodes 85A-D on its top surface and electrodes 85E-H on its bottom surface, and lower level 83B carries electrodes 85I-L on its top surface and electrodes 85M-P on its bottom surface. As a result, multiple level lead 81 may selectively deliver neurostimulation to any one or more of tissue 102A, 102B, and 102C.

Each of electrodes 85A-P are electrically isolated from each other and, thus, electrode combinations may be selected to deliver stimulation, such as PNFS, to any desired one or more of tissue layers 102A, 102B, and 102C. However, in other embodiments, electrodes on different surfaces of the levels may be electrically coupled in the manner discussed above with reference to FIG. 2C. Such coupling may simplify the structure and manufacturing of a multiple level lead.

Figure 5:
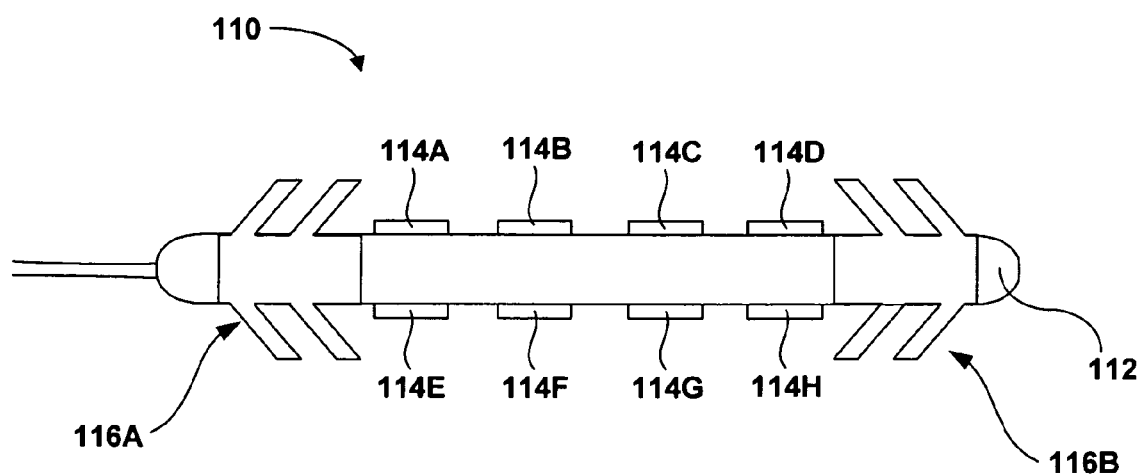
FIG. 5 is a schematic diagram illustrating an example implantable medical lead including fixation structures in accordance with an embodiment of the invention.

FIG. 5 is a schematic diagram illustrating a lead 110 that includes fixation structures. Lead 110 includes a lead body 112 at its distal end that carries electrodes 114A-H (collectively referred to as "electrodes 114") on multiple surfaces. Lead 110 may be a dual-sided paddle lead in which lead body 112 has a substantially flat, paddle-like shape, and may be substantially similar to dual sided paddle lead 30 of FIGS. 2A and 2B. However, unlike dual sided paddle lead 30, dual sided paddle lead 110 includes fixation structures 116A and 116B for securing lead 110 that prevent lead 110 from migrating from the implantation site.

Fixation structures may protrude from lead body 112 to engage tissue proximate to the lead body, as illustrated in FIG. 5. Fixation structure 116 may comprise one or more of tines, barbs, hooks, actively or passively deployable fixation structures, or collapsible or expandable fixation structures. Fixation structures may include titanium, stainless steel, nitinol, hydrogel, or any of a variety of materials. Tines, barbs and hooks may pierce tissue proximate to lead 110 to prevent migration after implantation. Tissue ingrowth surrounding tines or barbs may further secure lead 110.

When not acted upon by a force, collapsible structures assume an expanded configuration with the fixation structures extending away from lead body 112. However, when inserted into an insertion device, such as a needle, the collapsible fixation structures move close to lead body 118 assuming a collapsed configuration. When lead 110 is expelled from the insertion device, the fixation structures move toward their expanded positions.

Actively deployable fixation structures may include one or more actively deployable clips which, upon deployment, provides fixation of the lead to tissue proximate to the lead. The clip may be deployed in a variety of ways, such as releasing the clip from a restraint using a surgical tool or releasing the clip upon passage of the lead through body tissue to prevent withdrawal of the lead from body tissue. In this manner, protruding fixation structures 116A and 116B may enable a less complicated and time consuming method for securing a paddle lead, such as dual sided paddle lead, a multiple level lead, or a paddle lead known in the nerve stimulation field, to tissue to prevent migration. In some embodiments, the clips may be rounded or included needles. Other embodiments may include any type of fixation mechanism used to fix cardiac leads.

Figure 6:
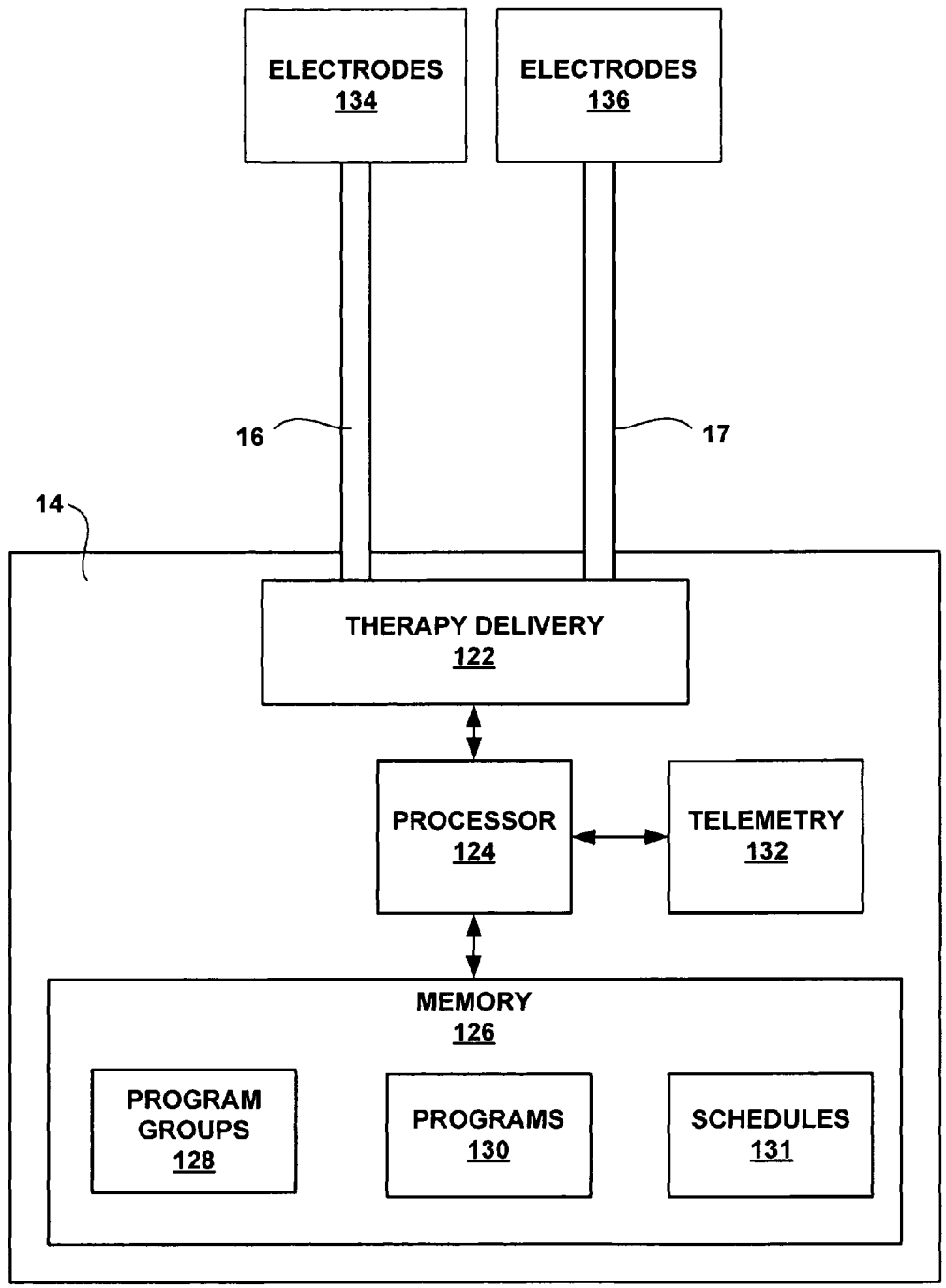
FIG. 6 is a block diagram illustrating the system of FIG. 1 in further detail.

In some embodiments, dual sided paddle lead 110 may only include protruding fixation structures 116B or 116A, i.e., may only include protruding fixation structures on a distal or a proximal end. Accordingly, FIG. 6 is merely exemplary and should not be considered limiting of the invention as broadly described in this disclosure. For example, protruding fixation structures 116A and 116B may be implemented with paddle leads that include electrodes on only a single surface. Protruding fixation structures located at the distal end of such paddle leads may offer similar advantages as described with respect to dual sided paddle lead 110. Further, fixation structures may be provides on multiple level leads as described herein. In some embodiments, fixation structures may be provided generally within the plane of the paddle lead. Alternatively, the fixation structures may be deployable after implantation.

FIG. 6 is a block diagram illustrating an example configuration of IMD 14. IMD 14 may deliver neurostimulation, such as PNFS, via electrodes 134 of lead 16 in combination with another type of stimulation, such as SCS, via and electrodes 136 of lead 17. Lead 16 may have electrodes on multiple surfaces, e.g., may be a dual sided paddle lead or a multiple level lead, as described in this disclosure. Lead 17 may be a lead as described herein or any type of known lead.

Electrodes 134 and 136 are electrically coupled to a therapy delivery module 122 via leads 16 and 17, respectively. Therapy delivery module 122 may, for example, include an output pulse generator coupled to a power source such as a battery. Therapy delivery module 122 may deliver electrical pulses to patient 12 via at least some of electrodes 134 and 136 under the control of a processor 124.

Processor 124 controls therapy delivery module 122 to deliver PNFS and another type of neurostimulation according to a selected one of program groups 128 stored in a memory 126. Specifically, processor 124 may control circuit 122 to deliver electrical pulses with the amplitudes, pulse widths, frequency, or electrode polarities specified by programs 130 of the selected program group 128, and according to the duty cycles specified by the programs. In the case of drug therapy, programs 130 may specify the amount, concentration, and rate of drug delivery. Programs 130 are also stored in memory 126.

In either case, each program group 128 may include programs 130 for peripheral neurostimulation only, another therapy only, or programs for both peripheral neurostimulation and the other therapy. Thus, processor 124 may control whether peripheral neurostimulation, another therapy, or both are delivered at any given time through selection of one of program groups 128. Similarly, a clinician or patient 12 using programmers 20, 26 to communicate with processor 124 via a telemetry module 132 may select delivery of peripheral neurostimulation, another therapy, or both through selection of one of program group 48.

Processor 124 may control therapy delivery module 122 to deliver programs 130 of a program group 48, and thus PNFS and another therapy, simultaneously. Processor 124 may control module 122 to interleave delivery of the programs 130 of the currently selected one of program groups 128 by delivering each successive stimulation pulse according to a different one of the programs. Further, the duty cycles of the respective programs 130 of the currently selected one of program groups 128 may be such that processor 124 controls therapy delivery module 122 to deliver the programs in an alternating manner.

Memory 126 may also store schedules 131. Schedules 131 may define times for processor 124 select a particular program 130 or program group 128, and control therapy delivery module 122 to deliver therapy according to that program or group. A schedule 131 may cause peripheral neurostimulation and at least one other therapy to be delivered at respective times, which may include simultaneous and/or alternate delivery. A clinician or patient may create, modify, and select schedules 131 using programmers 20, 26.

Through interleaved delivery of programs 130, different duty cycles or pulse rates of programs, schedules 131, and patient selection of programs 130 or program groups 128, therapy delivery module 122 may deliver PNFS and at least one other therapy in a generally alternating fashion. For example, electrical pulses may be interleaved so as to deliver the same frequency of electrical pulses for PNFS and the other types of therapy, but with varying amplitudes or pulse widths. As another example, a packet of pulses may be delivered to provide PNFS, with or without ramping of amplitude from start to finish, followed by delivering a packet of pulses to provide one of the other types of therapy. As a result, the likelihood that neural accommodation will impair the efficacy of one or more of the therapies will be reduced, while still providing therapy at any given time. Interleaved or alternating delivery of PNFS and one or more other electrical stimulation therapies may also prevent overuse or depletion of transmitters, such as GABA-B, that are major inhibitory transmitters released in the dorsal horn when electrical stimulation produces pain relief.

In addition to program groups 128, constituent programs 130 and schedules 131, memory 126 may include program instructions that, when executed by processor 124, cause IMD 14 and processor 124 to perform the functions ascribed to IMD 14 herein. Memory 126 may include any volatile, non-volatile, magnetic, optical, or electrical media, such as a random-access memory (RAM), read-only memory (ROM), non-volatile RAM (NVRAM), electronically-erasable programmable ROM (EEPROM), flash memory, or the like. Processor 124 may include any one or more of a microprocessor, digital signal processor (DSP), application specific integrated circuit (ASIC), field-programmable gate array (FPGA), discrete logic circuitry, or the like.

IMD 14 also includes a telemetry circuit 132 that allows processor 124 to communicate with clinician programmer 20 and patient programmer 26. Processor 124 may receive programs to test on patient 12 from clinician programmer 20 via telemetry circuit 132 during programming by a clinician. Processor 124 may receive programs 130, program groups 128 and schedules 131 from clinician programmer 20 via telemetry circuit 132 during programming by a clinician, and later receive program, program group, and schedule selections or modifications made by patient 12 from patient programmer 26 via telemetry circuit 132. In embodiments in which patient programmer 26 stores the program groups, rather than memory 126 of IMD 14, processor 124 may receive programs or groups selected by patient 12 from patient programmer 26 via telemetry circuit 132.

Figure 7:
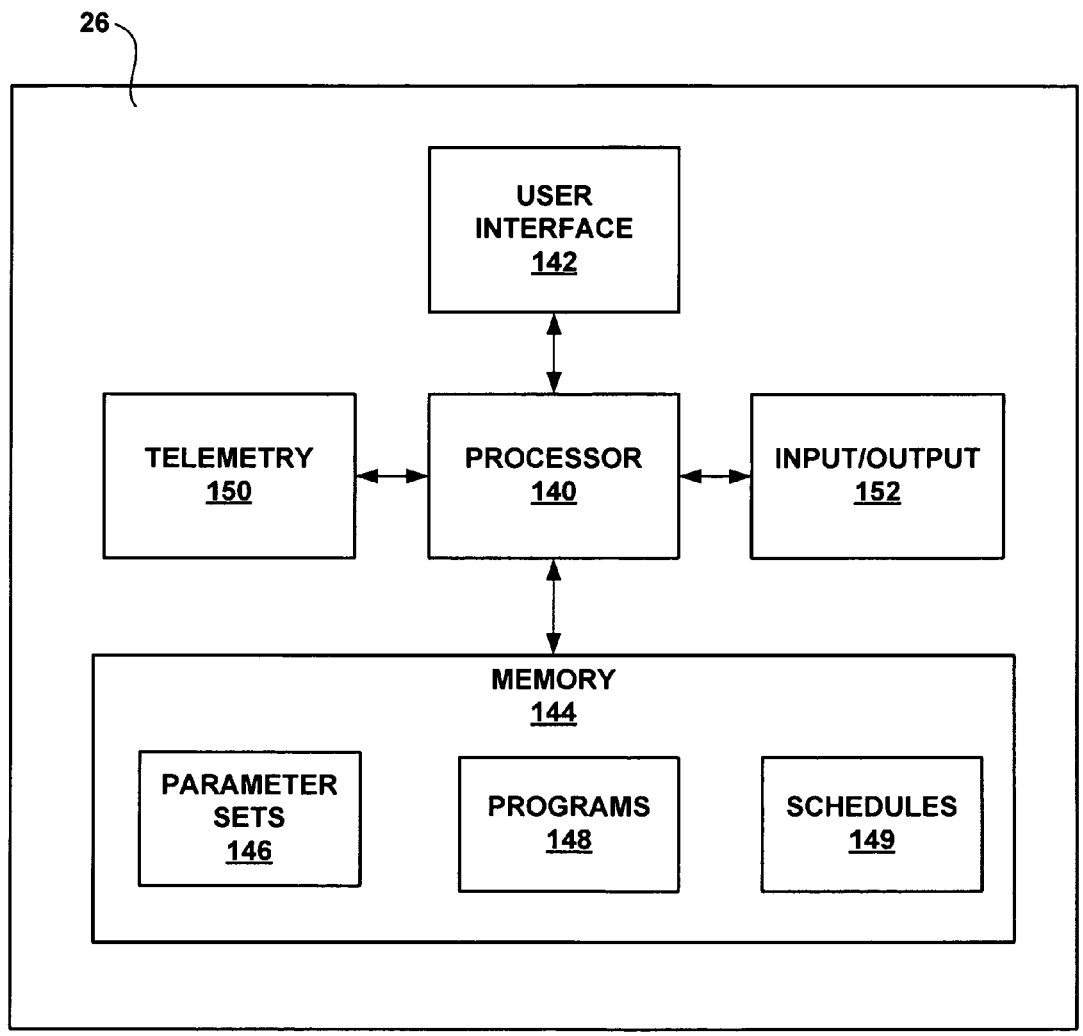
FIG. 7 is a block diagram illustrating an example clinician programmer that allows a clinician to program neurostimulation and one or more other types of therapy for a patient.

FIG. 7 is a block diagram illustrating an example configuration of patient programmer 26. Patient 12 may interact with a processor 140 via a user interface 142 in order to control delivery of peripheral neurostimulation in combination with one or more other types of therapy. User interface 142 may include display 28 and keypad 29, and may also include a touch screen or peripheral pointing devices as described above. Processor 140 may also provide a graphical user interface (GUI) to facilitate interaction with patient 12. Processor 140 may include a microprocessor, a controller, a DSP, an ASIC, an FPGA, discrete logic circuitry, or the like.

Patient programmer 26 also includes a memory 144. In some embodiments, memory 144 may store program groups 146 and programs 148 that are available to be selected by patient 12 for delivery of PNFS and one or more other types of therapy. Memory 144 may also store schedules 149 in similar fashion as memory 126 of IMD 14 (FIG. 6). Memory 144 may also include program instructions that, when executed by processor 140, cause patient programmer 26 to perform the functions ascribed to patient programmer 26 herein. Memory 144 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Patient programmer 26 also includes a telemetry circuit 150 that allows processor 140 to communicate with IMD 14, and input/output circuitry 152 that to allow processor 140 to communicate with clinician programmer 20. Processor 140 may receive program or program group selections made by patient 12 via user interface 142, and may either transmit the selection or the selected program or group to IMD 14 via telemetry circuitry 150 for delivery of stimulation according to the selected program or group. Further, processor 140 may select a program group 148 or programs 149 according to a schedule 149, and may either transmit the selection or the selected program or group to IMD 14 via telemetry circuitry 150 for delivery of stimulation according to the selected program or group. Where patient programmer 26 stores program groups 146 and programs 148 in memory 144, processor 140 may receive program groups 146 and programs 148 from clinician programmer 20 via input/output circuitry 152 during programming by a clinician. Circuitry 152 may include transceivers for wireless communication, appropriate ports for wired communication or communication via removable electrical media, or appropriate drives for communication via removable magnetic or optical media.

Figure 8:
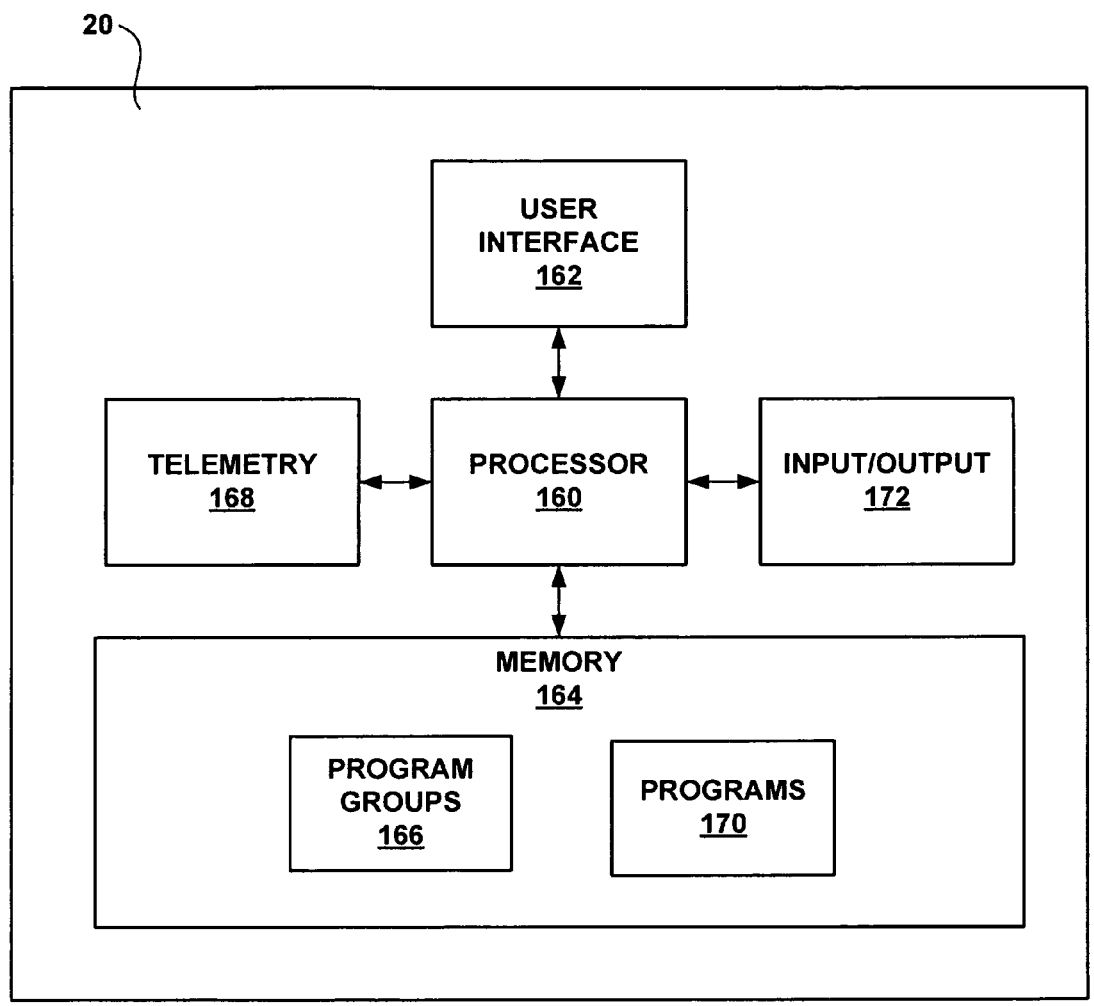
FIG. 8 is a block diagram illustrating an example patient programmer that allows a patient to control delivery of neurostimulation and one or more other types of therapy.

FIG. 8 is a block diagram illustrating an example configuration of clinician programmer 20. A clinician may interact with a processor 160 via a user interface 162 in order to program delivery of PNFS or other stimulation in combination with one or more other types of therapy. User interface 162 may include display 22 and keypad 24, and may also include a touch screen or peripheral pointing devices as described above. Processor 160 may also provide a graphical user interface (GUI) to facilitate interaction with a clinician, as will be described in greater detail below. Processor 160 may include a microprocessor, a controller, a DSP, an ASIC, an FPGA, discrete logic circuitry, or the like.

Clinician programmer 20 also includes a memory 164. Memory 164 may include program instructions that, when executed by processor 160, cause clinician programmer 20 to perform the functions ascribed to clinician programmer 20 herein. Memory 164 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program delivery of PNFS and one or more types of therapy for patient 12 by specifying a program group 166 or program 170 to test on patient 12. The clinician may interact with the GUI and user interface 162 in order to specify program groups or programs. Processor 160 transmits the selected or specified programs to IMD 14 for delivery to patient 12 via a telemetry circuit 168. Processor 160 may transmit program groups 166 and programs 170 created by the clinician to IMD 14 via telemetry circuitry 168, or to patient programmer 26 via input/output circuitry 172. I/O circuitry 172 may include transceivers for wireless communication, appropriate ports for wired communication or communication via removable electrical media, or appropriate drives for communication via removable magnetic or optical media.

Figure 9A:
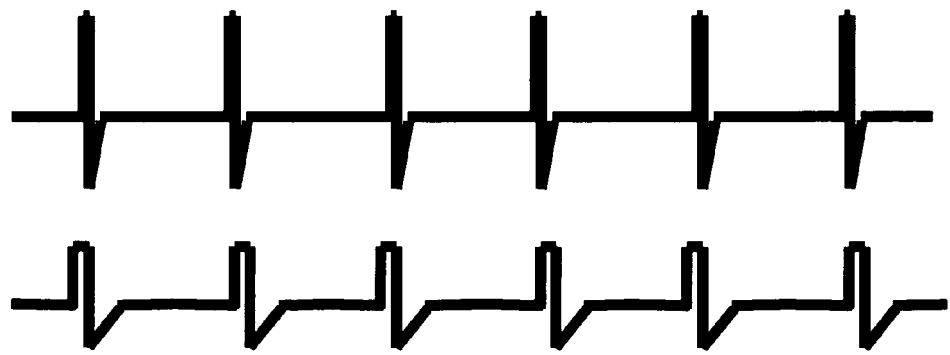
FIGS. 9A-9F are timing diagrams illustrating delivery of stimulation therapies in combination.
Figure 9B:
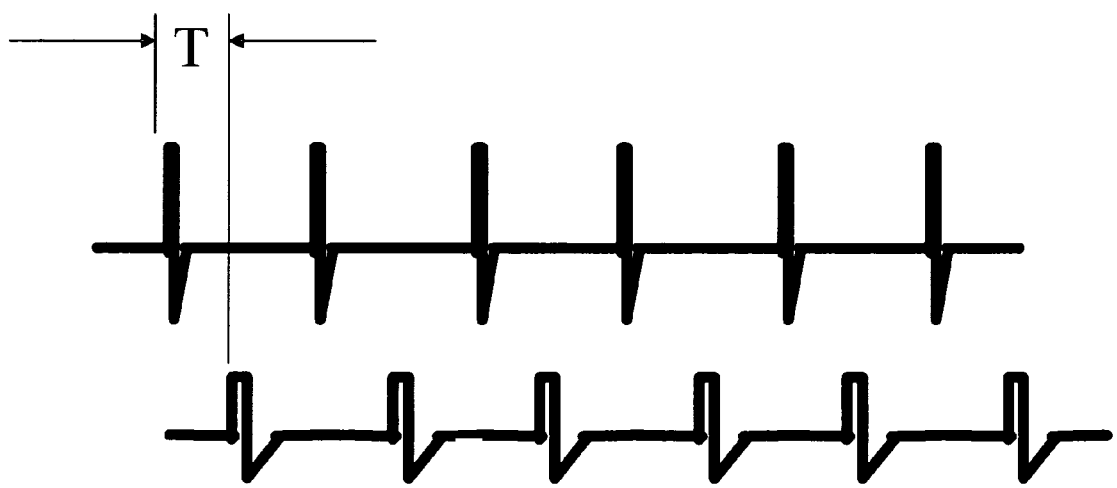
Figure 9C:
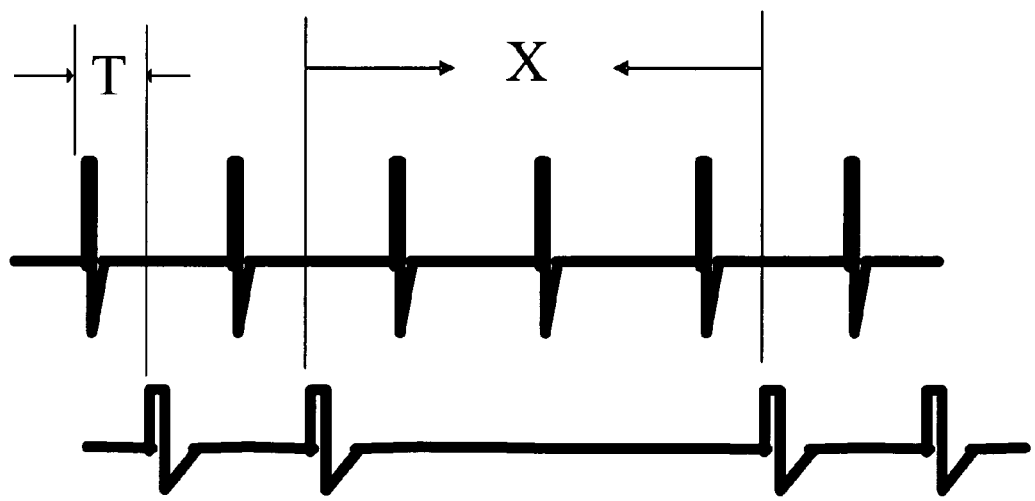
Figure 9D:
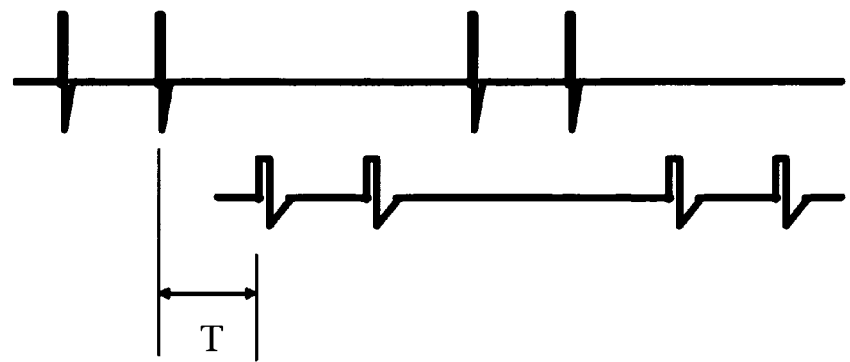
Figure 9E:
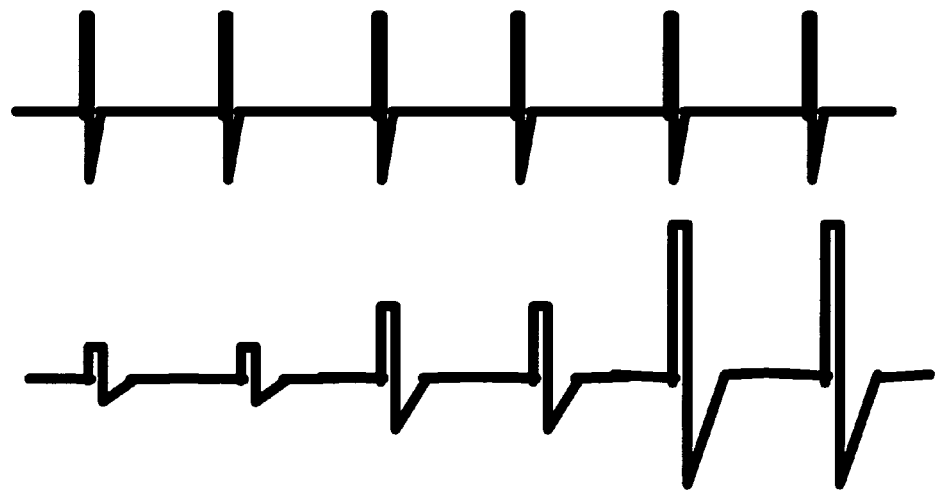
Figure 9F:
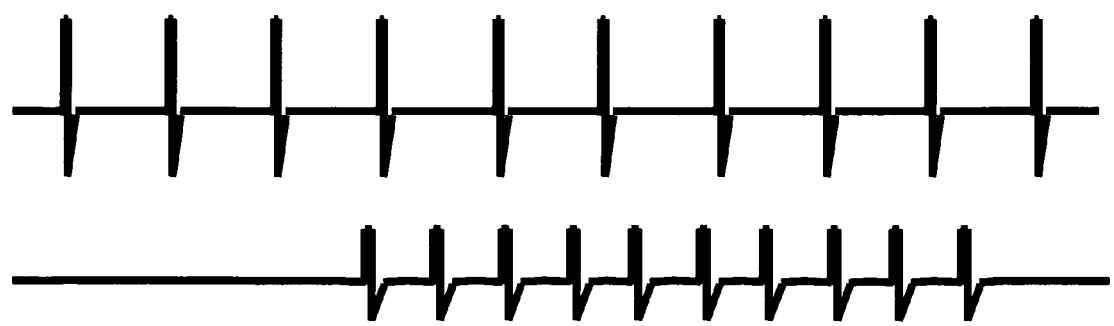

FIGS. 9A-9F are timing diagrams illustrating delivery of PNFS in combination with another neurostimulation therapy according to embodiments of the invention. SCS, PNS, DBS, and CS are examples of other types of stimulation therapies that may be delivered in combination with PNFS. In general, IMD 14 may deliver electrical pulses according to each of the therapies simultaneously, in an interleaved or alternating fashion, or overlapping in some degree in time. For example, each electrical stimulation therapy may have different pulse rates, duty cycles, or scheduled times for delivery, or IMD may deliver programs of a program group in an interleaved fashion, each of which may result in an alternating delivery of the therapies. In each of FIGS. 9A-9E, the bottom group of pulses represents delivery of PNFS pulses by IMD 14, and the top group of pulses represents delivery of another neurostimulation therapy, such as SCS, by the IMD. In FIG. 9F, the top group of pulses represents delivery of peripheral neurostimulation pulses by IMD 14, and the bottom group of pulses represents delivery of another neurostimulation therapy, such as DBS, by the IMD. Each group of pulse may represent delivery of pulses by IMD 14 according to a respective therapy program, and both groups of pulses may be included in a common program group.

FIG. 9A illustrates simultaneous delivery of peripheral neurostimulation, such as PNFS, and another neurostimulation therapy at a common pulse rate of 50 Hz by IMD 14. However, the PNFS and other neurostimulation are delivered with different amplitudes and pulse widths. Specifically, in the example illustrated by FIG. 9A, pulse for the other neurostimulation is delivered with a pulse amplitude and pulse width of 3 volts and 150 μs, respectively, and PNFS pulses are delivered at a pulse amplitude and pulse width of 2 volts and 300 μs, respectively.

FIG. 9B illustrates interleaved delivery of peripheral neurostimulation, such as PNFS, and another neurostimulation therapy by IMD 14 at the common pulse rate and different pulse amplitudes and widths illustrated by FIG. 9A. Interleaved delivery of PNFS pulses and pulses for the other neurostimulation resulting in a phase offset represented by a time T.

As was the case with FIG. 9B, FIG. 9C illustrates interleaved delivery of peripheral neurostimulation, such as PNFS, and another neurostimulation therapy by IMD 14 at the common pulse rate and different pulse amplitudes and widths illustrated by FIG. 9A. However, in the example illustrated by FIG. 9C, IMD 14 delivers PNFS with according to a duty cycle, rather than continuously. As a result, PNFS and the other neurostimulation are delivered for in an interleaved fashion similar to FIG. 9B for a period of time, followed by an equal period of time in which only the other neurostimulation is delivered.

FIG. 9D illustrates delivery of both peripheral neurostimulation, such as PNFS, and the other neurostimulation according to respective duty cycles, where the duty cycles result in alternating delivery of PNFS and the other neurostimulation.

FIG. 9E illustrates an example in which IMD 14 increases, e.g., "ramps up," the pulse amplitude of peripheral neurostimulation over time. In particular, FIG. 5E illustrates a pulse amplitude increase every two pulses FIG. 9F illustrates delivery of peripheral neurostimulation, such as PNFS, and another neurostimulation therapy by IMD according to different therapy parameters. In particular, IMD 14 delivers pulses for PNFS (top) at a frequency, amplitude, and pulse width of 40 Hz, 4.8 volts, and 400 μs, respectively, and pulse for the other neurostimulation therapy (bottom) at a frequency, amplitude, and pulse width of 240 Hz, 2 volts, and 140 μs, respectively.

Figure 10:
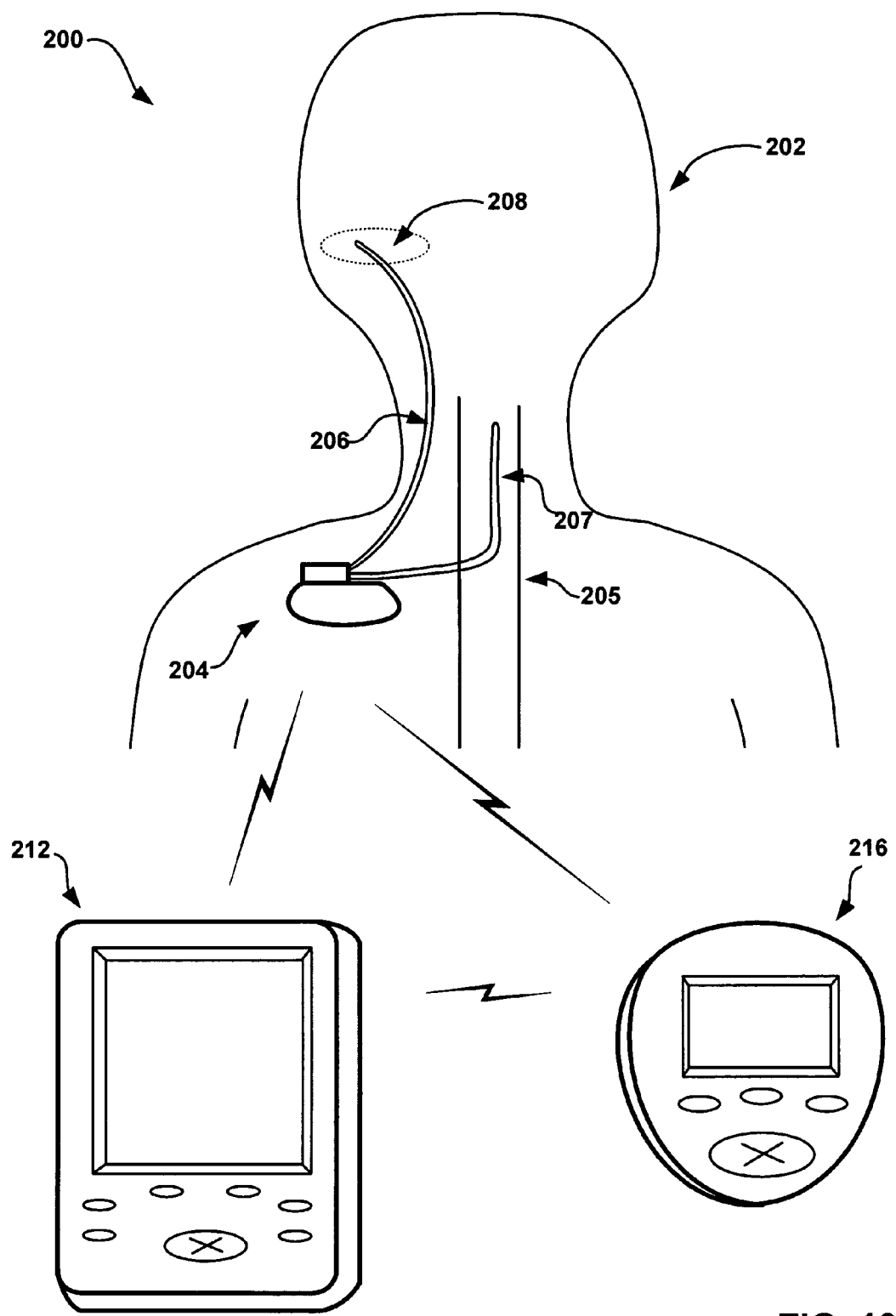
FIG. 10 is a conceptual diagram illustrating another example system for delivering stimulation to a patient.

FIG. 10 is a diagram illustrating another example system 200 for delivering stimulation, such as PNFS, in combination with another therapy to patient 202. In particular, like system 10 of FIG. 1, system 200 of FIG. 10 delivers PNFS in combination with SCS. However, unlike system 10, system 200 delivers PNFS to a region 208 on the face of a patient 205 where the patient experiences pain, and SCS to a region at the level of the C1-C3 vertebrae 205 of patient 202. The PNFS may, for example, alleviate supra-orbital or suborbital facial pain, while the SCS provides paresthesia to the back of the head and neck to alleviate, for example, headaches or migraines. In this manner, system 200 may more completely address a complex pain than would be possible through delivery of PNFS of SCS alone.

System 200 includes an IMD 204 coupled to leads 206 and 207 that include electrodes, which are substantially similar to and perform substantially similar functions as IMD 14 and leads 16 and 17 depicted and described above with reference to FIG. 1. System 200 may also include clinician and patient programmers 212 and 216, respectively, which may be substantially similar to and perform substantially similar functions as programmers 20, 26 depicted and described above with reference to FIGS. 1, 7 and 8. IMD 204 may deliver PNFS and SCS according to respective programs 130 of program groups 228, according to different therapy parameter values, and in a simultaneous, interleaved, or alternating fashion, in any of the manners described above.

Figure 11:
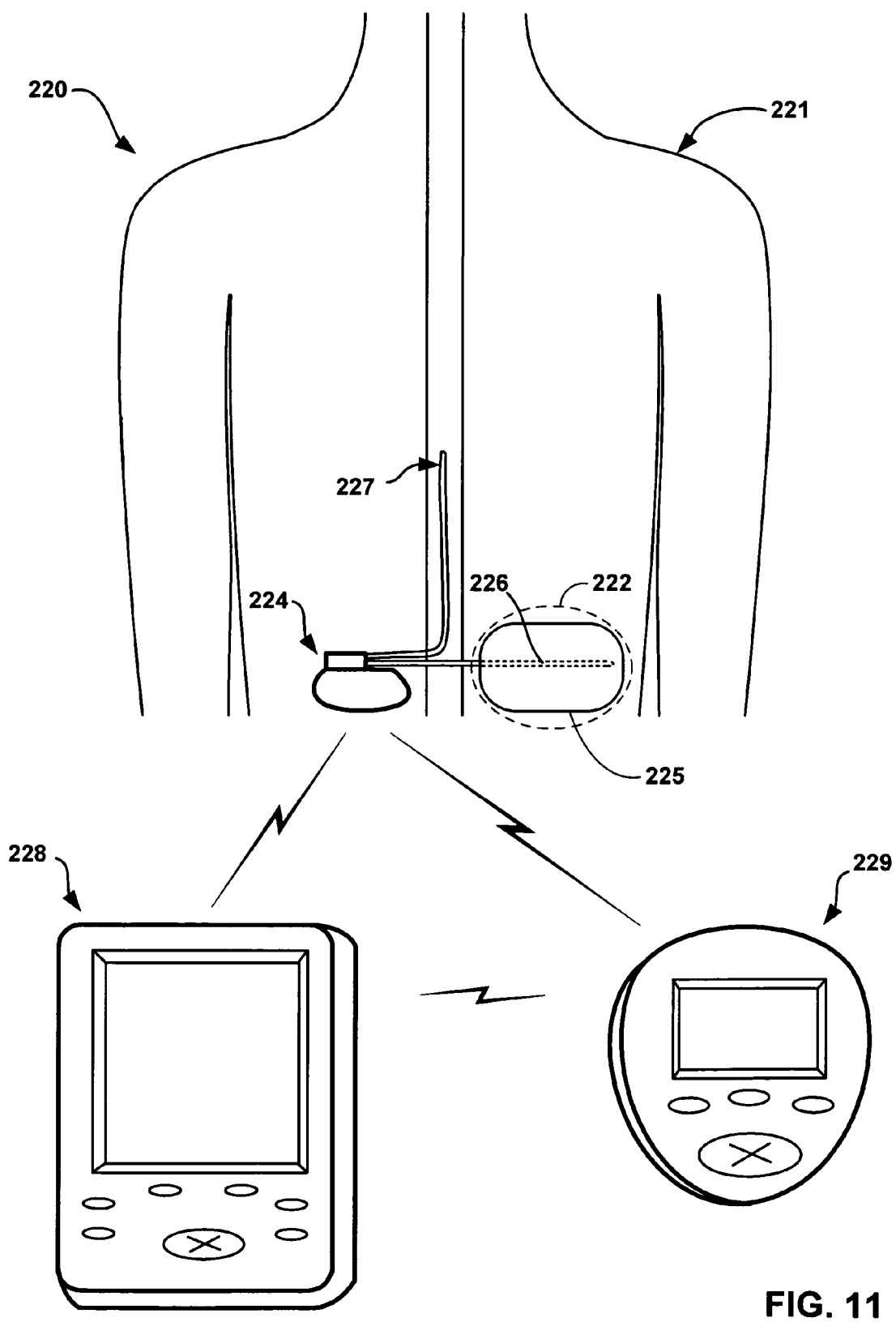
FIG. 11 is a conceptual diagram illustrating another example system for delivering stimulation to a patient.

FIG. 11 is a diagram illustrating another example system 220 for delivering stimulation, such as PNFS, in combination with at least one other therapy. More particularly, in the illustrated example, system 220 delivers PNFS to a region 222 where a patient 221 experiences pain, in combination with SCS and drug therapies. System 220 includes an IMD 224 that delivers PNFS and SCS via electrodes located on leads 226 and 227, respectively. Alternatively, separate IMDs may deliver PNFS and SCS. In such embodiments, the IMDs may communicate to coordinate therapy, e.g., wirelessly via radio frequency or electrical conduction through the body of patient 221. In the illustrated embodiment, drug therapy is also delivered to patient 221 at site 222 where pain is experienced by a patch 225 through which patient 221 transdermally absorbs a drug. Patch 225 is an example of an external medical device that delivers a therapy to patient 221.

For example, IMD 224 may deliver PNFS in combination with SCS and drug therapy in the manner illustrated by FIG. 7 for treatment of failed back surgery syndrome (FBBS) in which patient 221 experiences both axial pain and radiculopathy down one or both legs. In particular, IMD 224 may deliver PNFS at site 222 to treat axial back pain and SCS to the dorsal columns or dorsal roots of the spinal cord to treat radicular pain. Patient 221 may absorb drugs through patch 225 at site 222 to further relieve pain experienced at site 222 or enhance the PNFS therapy. Consequently, system 220 may more completely address complex pain than would be possible through delivery of PNFS, SCS, or drug therapy alone.

Lead 226 may be implanted in intra-dermal, deep dermal, or subcutaneous tissues of patient. In the illustrated embodiment, lead 226 extends from IMD 224 to the lower back of patient 221 to relieve pain, e.g. axial back pain, in region 222. Lead 227 may extend from IMD 224 over the dorsal roots at vertebral levels L3-S1 or over dorsal columns at vertebral levels T10-L1 to relieve radicular pain in one or both legs. IMD 224 may deliver PNFS and SCS simultaneously, or in interleaved or alternating fashion. Interleaved or alternating delivery of PNFS and SCS may reduce the likelihood that neural accommodation will impair the efficacy of the therapies while still providing one of the therapies at any given time.

In addition, patch 225 delivers drug therapy to patient 221 at region 222. Patch 221 absorbs a drug through patch 225. However, the invention is not limited as such. In some embodiments drug therapy may be delivered orally, intrathecally, or extradurally. In additional embodiments, IMD 224 may also include a reservoir and drug pump to deliver the drug to region 222 or another location via a catheter. Examples of drugs that be used are opioids, cannabinoids, anti-inflammatory agents, steroids, baclofen, adenosine, local anesthesia, anti-depressants, and alpha agonists. Delivered drugs may, for example, diminish pain by their own action, especially when applied to specific sites, enhance the benefits of electrical stimulation, and treat particular pain modalities. Nociceptive pain may be treated through delivery of morphine, for example, and the action of specific nerves may be blocked through delivery of local anesthetics. Consequently, delivering PNFS in combination with drug therapy may more completely address complex pain than would be possible through the delivery of one of the other therapies alone. As one example of the synergy between therapies, PNFS delivered to region 222 by IMD 224 may reduce allodynia, thereby allowing patch 225 to be applied to the skin of patient 221 to deliver drug therapy.

System 220 includes an IMD 224 coupled to leads 226 and 227 that include electrodes, which are substantially similar to and perform substantially similar functions as IMD 14 and leads 16 and 17 depicted and described above with reference to FIG. 1. System 200 may also include clinician and patient programmers 228 and 229, respectively, which may be substantially similar to and perform substantially similar functions as programmers 20, 26 depicted and described above with reference to FIGS. 1, 7 and 8. IMD 224 may deliver PNFS and SCS according to respective programs 130 of program groups 128, according to different therapy parameter values, and in a simultaneous, interleaved, or alternating fashion, in any of the manners described above.

Table 1 below illustrates various combinations of PNFS therapy with other types of therapy to relieve pain associated with a number of conditions. In particular, each row of the table provides an "indication" that is treated, a location or "site" at which to deliver PNFS, reason(s) for delivering PNFS at the site, various sites at which to deliver other therapies and the reasons for delivering the other therapy types. The other types of therapy delivered in combination with PNFS include SCS, PNS, and various forms of DBS and CS. As used in Table 1, the acronyms PVG and PAG refer to midbrain gray matter stimulation locations, and the acronyms VPL and VPM refer to thalamic stimulation location. More particularly, PVG, PAG, VPL and VPM respectively refer to a preventricular gray, periaqueductal gray, ventroposterior lateral nucleus and ventral posterior medial nucleus stimulation locations.

For example, PNFS may be delivered in combination with SCS, PNS, DBS and/or CS to treat axial back pain. In this case, approximately one to four leads having approximately four to sixty-four electrodes may be implanted in the intradermal, deep-dermal, or subcutaneous tissue at region where the patient experiences pain. SCS may be delivered to the T7-T10 vertebral levels in combination with PNFS to give paresthesia into the back. PNS may be delivered to a branch of the median nerve in combination with PNFS to treat facet pain that the patient may experience in addition to the axial back pain. DBS may be delivered to PVG, PAG, or VPL locations in combination with PNFS to treat neuropathic components of the pain. CS may also be delivered to the motor cortex, near the midline in combination with PNFS to treat neuropathic components.

As another example, PNFS may be delivered in combination with SCS, DBS and/or CS to treat occipital neuralgia and headaches. In this case, electrode groups for PNFS may be implanted in a line transverse to the C2 and C3 nerve branches. Fascia, muscle, or tendons may be between the groups of electrodes and the nerves in order reduce the likelihood of unpleasant stimulation. SCS may be delivered to the C1-C3 nerves in combination with PNFS to give paresthesia into the back. DBS may be delivered to PVG, PAG, or VPM locations in combination with PNFS to treat neuropathic components of the pain, or triggers of the migraines. CS may be delivered to the lateral part of the motor cortex in combination with PNFS to also treat neuropathic components or triggers.

In another example, PNFS may be delivered in combination with PNS, DBS and/or CS to treat temporomandibular joint pain. In this case, electrodes for PNFS may be implanted in front of the ear to deliver stimulation to or near the region where the patient experiences pain. PNS may be delivered to branches of the trigeminal nerve (V), including delivering PNS in the Gasserian ganglia foramen, in combination with PNFS to relieve neuropathic pain. DBS may be delivered to PVG, PAG, or VPM locations in combination with PNFS to give paresthesia into the face of the patient. CS may be delivered to the lateral part of the motor cortex in combination with PNFS to treat neuropathic components of the pain.

A common patient problem for stimulation therapies today is a combination of axial back pain and radiculopathy, which is often a form of failed back surgery syndrome (FBBS). In a further example, PNFS may be delivered in combination with SCS, PNS, DBS and/or CS to treat FBBS. SCS can work very well for the radiculopathy, especially for the lower limbs, but its success for the axial pain can be less, especially after six or more months. In this case, PNFS in the painful areas of the back can help the axial pain, and the SCS part of the combined system can deal well with the radicular symptoms.

The following combination of therapies may provide relief from axial pain and radiculopathy associated with FBBS. In this case, 1-4 electrode leads having 4-64 electrodes may be implanted in intra-dermal, deep-dermal, or subcutaneous tissue in a region where the patient experiences pain for delivery of PNFS. SCS may be delivered to the T7-T10 vertebral levels as well as the T10-L1 vertebral levels in combination with PNFS to give paresthesia into the back, leg, and/or foot. DBS may be delivered to PVG, PAG, or VPL locations in combination with PNFS to treat neuropathic components of the pain. CS may be delivered near the midline of the motor cortex in combination with PNFS to treat neuropathic components or triggers.

In yet another example, PNFS may be delivered in combination with SCS, DBS and/or CS to treat supra-orbital or sub-orbital facial pain. In this case, electrode groups for PNFS may be implanted in a line above or below the eye, e.g., roughly parallel to the eyebrow, to deliver stimulation to branches of the facial nerve (VIII). In this case, SCS may be delivered to the C1-C3 nerves in combination with PNFS to give paresthesia into the back of the head and neck. DBS may be delivered to PVG, PAG, or VPM locations in combination with PNFS to treat neuropathic components or triggers. CS may be delivered to the lateral part of the motor cortex in combination with PNFS to treat neuropathic components or triggers.

In a further example, PNFS may be delivered in combination with SCS, PNS, DBS and/or CS to treat arthritis. In this case, electrode groups may be implanted in intra-dermal, deep-dermal, or subcutaneous tissue in any region where the patient experiences arthritis pain. SCS may be delivered to the C4-C8 vertebral levels for upper limb pain and to the T10-L1 vertebral levels for hip, knee, ankle and foot pain in combination with PNFS to give paresthesia into the painful area. PNS may be delivered to an appropriate major arm or leg nerve in combination with PNFS to give paresethesia into the painful area. DBS may be delivered to PVG, PAG, or VPL locations in combination with PNFS to treat neuropathic components or triggers. CS may be delivered near the midline of the motor cortex in combination with PNFS to treat neuropathic components in the leg and feet. CS may also be delivered near the lateral part of the motor cortex in combination with PNFS to treat neuropathic components in the arm and hand.

In another example, PNFS may be delivered in combination with SCS, PNS, DBS and/or CS to treat inguinal pain. In this case, electrode groups may be implanted in intra-dermal, deep-dermal, or subcutaneous tissue in any region where the patient experiences pain to give nonpainful PNFS stimulation to the painful area. SCS may be delivered to the T4-L1 vertebral levels in combination with PNFS to give paresthesia into the painful area. PNS may be delivered via electrodes implanted deeper along the nerves involved in the pain in combination with PNFS to give paresethesia into the painful area. DBS may be delivered to PVG, PAG, or VPL locations in combination with PNFS to treat neuropathic components or triggers. CS may be delivered near the midline of the motor cortex in combination with PNFS to treat neuropathic components in the leg and feet.

In another example, PNFS may be delivered in combination with SCS, PNS, DBS and/or CS to treat a form of arthritis. In this case, electrode groups may be implanted in intra-dermal, deep-dermal, or subcutaneous tissue in any region where the patient experiences pain to give nonpainful PNFS stimulation to the painful area. SCS may be delivered to the T8-L1 vertebral levels in combination with PNFS to give paresthesia into the painful area. PNS may be delivered to the pudendal nerve in combination with PNFS to treat neuropathic components. DBS may be delivered to PVG, PAG, or VPL locations in combination with PNFS to treat neuropathic components or triggers. CS may be delivered near the midline of the motor cortex in combination with PNFS to treat neuropathic components in the lower body.

In another example, PNFS may be delivered in combination with SCS, PNS, DBS and/or CS to treat angina, or pain associated with other heart dysfunction, such as arrhythmia. In this case, electrodes may be implanted over the heart, any part of the thorax or at any region where the patient experiences pain, such as in the arms, jaw, or back. For example, electrodes may be implanted within or between intra-dermal, deep dermal, or subcutaneous tissues of the chest. Delivering PNFS in this manner may reduce angina attacks. SCS may be delivered to the C1-T4 vertebral levels in combination with PNFS to give paresthesia into the painful area and reduce angina. PNS may be delivered to the vagus nerve in combination with PNFS to slow the heart and, thus, reduce stress on the heart. DBS may be delivered to PVG, PAG, or VPL locations in combination with PNFS to treat neuropathic components. DBS may also be delivered to nuclei near the hypothalamus or in the ventral lateral medulla in combination with PNFS to lower blood pressure, which may reduce pain by reducing the stress on the heart. CS may be delivered several centimeters off the midline of the motor cortex in combination with PNFS to treat neuropathic components.

In yet another example, PNFS may be delivered in combination with SCS, PNS, DBS and/or CS to treat cancer pain or phantom limb pain. In this case, electrode groups may be implanted in intra-dermal, deep-dermal, or subcutaneous tissue in a region where the patient experiences pain to give nonpainful stimulation to the painful region. SCS may be delivered at a level appropriate to the pain experienced by the patient in combination with PNFS to give paresthesia into the painful area. PNS may be delivered to a nerve involved in the pain in combination with PNFS to treat neuropathic components of the pain. DBS may be delivered to PVG, PAG, VPL, or VPM locations in combination with PNFS to treat neuropathic components or triggers. CS may be delivered at an appropriate location of the motor cortex in combination with PNFS to treat neuropathic components of the pain

TABLE 1

| Indication | Site for PNFS | Reason for Delivering PNFS | Site for other Therapy | Reason for Delivering Other Therapy |
|---|---|---|---|---|
| Axial back pain | Axial back, 1-4 leads, 4-64 electrodes | Deliver stimulation to the region where patient experiences pain | SCS: T7-T10 | Gives paresthesia into the back |
|  |  |  | PNS: branch of median nerve | Also treat facet pain |
|  |  |  | DBS: PVG or PAG | Treat nociceptive components |
|  |  |  | DBS: VPL | Treat neuropathic components |
|  |  |  | CS: motor cortex, near midline | Treat neuropathic components |
| Occipital neuralgia, headaches | Electrode groups in a line transverse to the C2 and C3 nerve branches | Deliver stimulation to the C2 and C3 nerves to prophylactically prevent migraines and headaches | SCS: C1-C3 | Gives paresthesia into the back |
|  |  |  | DBS: PVG or PAG | Treat nociceptive components |
|  |  |  | DBS: VPM | Treat neuropathic components or triggers |
|  |  |  | CS: motor cortex, lateral part | Treat neuropathic componenets or triggers |
| Temporomandibular joint pain | In front of ear | Deliver stimulation to or near the pain site. May be desirable to avoid nerves in lower jaw | PNS: branches of the trigeminal nerve (V), including in the Gasserian ganglia foramen | Relieve neuropathic pain |
|  |  |  | DBS: PVG or PAG | Treat nociceptive components |
|  |  |  | DBS: VPM | Gives paresthesia into the face |
|  |  |  | CS: motor cortex, lateral part | Treat neuropathic components |
| Failed back surgery syndrome (axial pain and radiculopathy) | Axial back, 1-4 leads, 4-64 electrodes | Deliver stimulation where the patient experiences pain | SCS: T7-L1 | Gives paresthesia into the back and leg and/or foot |
|  |  |  | PNS: Branch of median nerve or along nerves in leg | Also treat facet join pain an neuropathies in the nerves in the leg |
|  |  |  | DBS: PNG or PAG | Treat nociceptive components |
|  |  |  | DBS: VPL | Treat neuropathic components |
|  |  |  | CS: motor cortex, near midline | Treat neuropathic components |

TABLE 1-continued

| Indication | Site for PNFS | Reason for Delivering PNFS | Site for other Therapy | Reason for Delivering Other Therapy |
|---|---|---|---|---|
| Supra-orbital or sub-orbital facial pain | Electrode groups in a line above or below the eye, roughly parallel to the eyebrow | Deliver stimulation to branches of the facial nerve (VIII) | SCS: C1-C3 | Gives paresthesia into the back of the head and neck |
| | | | DBS: PVG or PAG | Treat nociceptive components |
| | | | DBS: VPM | Treat neuropathic components |
| | | | CS: motor cortex, lateral part | Treat neuropathic components |
| Arthritis | Place electrodes in skin with the same dermatome as the painful area | Give nonpainful stimulation to the same nerves as those involved in pain | SCS: C4-C8 for upper limb pain; T1-L1 for hip, knee, ankle or foot pain | Gives paresthesia into the painful area which may lessen pain |
| | | | PNS: of the major arm or leg nerves | Gives paresthesia into the painful area which may lessen pain |
| | | | DBS: PVG or PAG | Treat nociceptive components |
| | | | DBS: VPL | Treat neuropathic components |
| | | | CS: motor cortex, near midline for leg and feet | Treat neuropathic components |
| Pelvic pain, and or visceral organ pain | Place electrodes in skin areas over any painful area | Give nonpainful stimulation to painful area | SCS: T8-L1 | Gives paresthesia into the painful area which may lessen pain |
| | | | PNS: Pudendal nerve | Treat neuropathic components |
| | | | DBS: PVG or PAG | Treat nociceptive components |
| | | | DBS: VPL | Treat neuropathic components |
| | | | CS: motor cortex, near midline for lower body | Treat neuropathic components |
| Angina, heart dysfunction, or arrhythmia | Electrodes over the heart part of the thorax or at any painful area, even in the arms, jaw, or back | Reduce angina attacks | SCS: C1-T4 | Gives paresthesia into the painful area which may lessen pain and reduce angina |
| | | | PNS: Vagus nerve, medial nerve, ulnar nerve | Slows heart, reducing stress on the heart |
| | | | DBS: PVG or PAG | Treat nociceptive components |
| | | | DBS: VPL | Treat neuropathic components |
| | | | DBS: Nuclei near the hypothalamus or in the ventral lateral medulla | Lowers blood pressure |
| | | | CS: motor cortex, several | Treat neuropathic |

TABLE 1-continued

| Indication | Site for PNFS | Reason for Delivering PNFS | Site for other Therapy | Reason for Delivering Other Therapy |
|---|---|---|---|---|
| Cancer or phantom limb pain | Place electrodes in skin areas over any painful area | Give nonpainful stimulation to painful area | centimeters off the midline SCS: at a level appropriate to the pain | components Gives paresthesia into the painful area which may lessen pain |
| | | | PNS: on a nerve appropriate to the pain | Treat neuropathic components |
| | | | DBS: PVG or PAG | Treat nociceptive components |
| | | | DBS: VPL or VBM | Treat neuropathic components |
| | | | CS: motor cortex, at a site appropriate for the painful area | Treat neuropathic components |

Table 2 below illustrates various drugs, one or more of which may be delivered in combination with PNFS, either alone or in combination with any of the other stimulation modalities indicated above. Drugs can delivered in combination with PNFS may allow complex or multifocal pain to be better addressed by: diminishing pain by their own action (additive effect), especially if applied to specific sites (patches, intrathecal, epidural); augmenting or magnifying the benefits of electrical stimulation; addressing certain types or locations of pain, such as morphine for nociceptive pain, or local anesthetics to block some nerves.

TABLE 2

| Drug | Delivery Site and Mechanism | Reason for Delivering |
|---|---|---|
| Opioid | Lumbar intrathecal space Systemic (oral, IV, fentanyl patch) Subcutaneous axial back (Permeable membrane catheter) Intracerebroventricular Intraparenchymal Local peripheral administration | Treat nociceptive aspects of pain |
| δ opioid | Systemic, ICV, IP, Local peripheral administration | Synergistic with high frequency stimulation |
| μ opioid | Systemic, ICV, IP, Local peripheral administration | Synergistic with low frequency stimulation |
| Cannabinoid | Lumbar intrathecal space Systemic (oral, IV) Subcutaneous axial back (Permeable membrane catheter) Intracerebroventricular Intraparenchymal Local peripheral administration | Treat nociceptive aspects of pain |
| Local anesthetic (e.g. Bupivacaine) | Lumbar intrathecal Epidural Lumbar sympathetic chain Vertebral disc Facet joint Patch infusion into axial back subcutaneous tissue Local peripheral | Additive effect for neuropathic pain |

TABLE 2-continued

| Drug | Delivery Site and Mechanism | Reason for Delivering |
|---|---|---|
| | administration | |
| Baclofen (GABA agonist) | Systemic Lumbar intrathecal Local peripheral administration | Potentiates neurostimulation |
| Adenosine | Systemic Lumbar intrathecal Local peripheral administration | Potentiates neurostimulation |
| α-adrenergic agonists (e.g. Clonidine) | Systemic Lumbar intrathecal Vertebral disc Facet joint Local peripheral administration | Potentiates neurostimulation Additive effect for neuropathic pain |
| Anti-inflammatory (e.g. NSAIDS, steroids, TNFα blocker) | Systemic Patch infusion into axial back SQ tissue Catheter infusion into SQ tissue Lumbar intrathecal Lumbar epidural Vertebral disc Facet joint Local peripheral administration | Reduce inflammation in addition to stimulation |
| Muscle relaxant | Systemic Patch infusion into axial back SQ tissue Catheter infusion into axial back SQ tissue Local peripheral administration | Relax back muscles in addition to stimulation |
| Antidepressant | Systemic ICV, IP Local peripheral administration | Additive to stimulation |
| Antiepileptic (e.g. Gabapentin) | Systemic ICV, IP Lumbar intrathecal Local peripheral administration | Additive to stimulation |

Many embodiments of the invention have been described. However, one of ordinary skill will recognize that various modifications may be made without departing from the scope of the claims. For example, although described herein with reference to PNFS, stimulation of intra-dermal, deep dermal or subcutaneous layers, and combination therapies, the invention is not so limited. Leads according to the invention may be used to deliver any stimulation therapy to any type of tissue at any location, alone, or in combination with other therapies. These and other embodiments are within the scope of the following claims.

The invention claimed is:

1. An implantable medical lead comprising:
   a lead body that comprises at least first and second separate lead body levels fixed in substantially parallel offset planes, each of the lead body levels including a substantially flat paddle-like three dimensional shape comprising a first major surface, a second major surface opposite the first major surface, and a plurality of electrodes, at least one of which is arranged on each of the first and the second major surfaces of the flat paddle-like three dimensional shape; and
   a fixation structure located at a distal end of the flat paddle-like three dimensional shape of at least one of the at least first and second separate lead body levels for securing the lead body to tissue of the patient.

2. The lead of claim 1, wherein the fixation structure protrudes from the lead body to engage tissue of the patient.

3. The lead of claim 1, wherein the fixation structure comprises at least one of a tine, a barb, a deployable structure, a collapsible structure, an expandable structure, or a hydrogel.

4. The lead of claim 1, wherein the at least first and second separate lead body levels comprises first and second separate lead body levels, and wherein the fixation structure is located at a distal end of the first lead body level.

5. An implantable medical lead comprising:
   a lead body that comprises at least first and second separate lead body levels fixed in substantially parallel offset planes, each of the lead body levels including a substantially flat paddle-like three dimensional shape comprising a first major surface, a second major surface opposite the first major surface, and a plurality of electrodes, at least one of which is arranged on each of the first and the second major surfaces of the flat paddle-like three dimensional shape; and
   a fixation structure that protrudes from the lead body to engage tissue of the patient for securing the lead body to the tissue.

6. The lead of claim 5, wherein the fixation structure comprises at least one of a tine, a barb, a deployable structure, a collapsible structure, an expandable structure, or a hydrogel.

7. The lead of claim 5, wherein the fixation structure protrudes from one or both of the first and the second separate lead body levels.

* * * * *